US012805697B2

(12) United States Patent
Sasai et al.

(10) Patent No.: US 12,805,697 B2
(45) Date of Patent: Nov. 24, 2026

(54) ENDOSCOPE SYSTEM, ENDOSCOPE MOVEMENT CONTROL METHOD, AND COMPUTER-READABLE RECORDING MEDIUM FOR ESTIMATING ROTATIONAL RELATIONSHIPS BASES ON IMAGE MOTION

(71) Applicant: OLYMPUS CORPORATION, Tokyo (JP)

(72) Inventors: Ryota Sasai, Tokyo (JP); Hiroyuki Takayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 219 days.

(21) Appl. No.: 18/670,108

(22) Filed: May 21, 2024

(65) Prior Publication Data

US 2024/0389830 A1 Nov. 28, 2024

Related U.S. Application Data

(60) Provisional application No. 63/468,906, filed on May 25, 2023.

(51) Int. Cl.

*A61B 1/00* (2006.01)
*A61B 1/05* (2006.01)
*A61B 34/30* (2016.01)

(52) U.S. Cl.

CPC ...... *A61B 1/00011* (2013.01); *A61B 1/00096* (2013.01); *A61B 1/05* (2013.01); *A61B 34/30* (2016.02); *A61B 2034/305* (2016.02)

(58) Field of Classification Search

CPC ... A61B 1/00011; A61B 1/00096; A61B 1/05; A61B 1/00149; A61B 1/0016;

(Continued)

(56) References Cited

U.S. PATENT DOCUMENTS 9,188,973 B2 11/2015 Tenney et al.
9,542,743 B2 1/2017 Tenney et al.

(Continued)

FOREIGN PATENT DOCUMENTS

WO 2013/009510 A2 1/2013
WO 2023/100234 A1 6/2023

OTHER PUBLICATIONS

Olympus Corporation of the Americas, "VEII 3D Rigid ENDOEYE Prism Tip Technology" (the entire video), URL:https://www.youtube.com/watch?v=NdaajF8ktXU; Nov. 13, 2020.

*Primary Examiner* — Anhtuan T Nguyen
*Assistant Examiner* — Li-Ting Song
(74) *Attorney, Agent, or Firm* — Scully, Scott, Murphy & Presser, P.C.

(57) ABSTRACT

An endoscope system includes an endoscope including an insertion portion, an imaging sensor disposed at a proximal end thereof so as to be rotatable about a longitudinal axis, and an optical element that tilts an optical axis, a robotic arm, and at least one processor. The processor transmits a first signal to the moving device, detects a first moving direction of an object, estimates a first amount of rotation of the optical element by using first two images before and after the transmission with respect to the imaging sensor based on the first movement direction, transmits a second signal to the robotic arm, detects a second moving direction of the object by using second two images before and after the transmission, and estimates a second amount of rotation between the robotic arm and the endoscope based on the second moving direction and the first amount of rotation.

20 Claims, 25 Drawing Sheets

(58) Field of Classification Search
CPC . A61B 1/042; A61B 1/00147; A61B 1/00179; A61B 34/30; A61B 2034/305; A61B 2034/2065; A61B 2090/067
See application file for complete search history.

(56) References Cited

U.S. PATENT DOCUMENTS

| | | | | |
|---|---|---|---|---|
| 2019/0008367 | A1* | 1/2019 | Ishikawa .............. | A61B 90/361 |
| 2019/0274524 | A1* | 9/2019 | Nagao ................ | A61B 1/00149 |
| 2021/0015346 | A1* | 1/2021 | Kuroda .............. | G02B 23/2484 |
| 2022/0408002 | A1* | 12/2022 | Birkenbach .......... | A61B 1/0016 |
| 2025/0176804 | A1* | 6/2025 | Tomatsu ................ | A61B 1/045 |

* cited by examiner

ENDOSCOPE SYSTEM, ENDOSCOPE MOVEMENT CONTROL METHOD, AND COMPUTER-READABLE RECORDING MEDIUM FOR ESTIMATING ROTATIONAL RELATIONSHIPS BASES ON IMAGE MOTION

CROSS-REFERENCE TO RELATED APPLICATIONS

This application claims the benefit of U.S. Provisional Application No. 63/468,906, filed May 25, 2023, which is hereby incorporated by reference herein in its entirety.

TECHNICAL FIELD

The present disclosure relates to an endoscope system, an endoscope movement control method, and a recording medium.

BACKGROUND

An endoscope system in which an endoscope is moved by a moving device such as an electric holder has been conventionally known. In order to move the endoscope accurately, it is desirable that the coordinate system of the endoscope and the coordinate system of the moving device match each other.

For example, when an operator remotely operates an electric holder using a user interface, the operator inputs a desired moving direction of the endoscope into a user interface based on an endoscopic image. When the coordinate system of the endoscope and the coordinate system of the moving device match each other, the user can intuitively and accurately move the endoscope in a desired direction. On the other hand, when the coordinate system of the endoscope and the coordinate system of the moving device do not match each other, the actual moving direction of the endoscope is different from the moving direction input to the user interface, which makes it difficult for the user to intuitively and accurately move the endoscope in a desired direction.

In a robot system in which a camera system is attached to a movable arm, there is known a method for correcting the transformation between the coordinate system of a robot and the coordinate system of a camera system (see, for example, PTL 1). In PTL 1, an image of a target is captured by a camera system, and the transformation is determined from the position of the movable arm when the image is captured and the position of a feature point of the target in the image.

SUMMARY

According to an aspect of the present disclosure, an endoscope system comprises: an insertion portion extending in a longitudinal axis direction;

an imaging sensor disposed at a proximal end of the insertion portion so as to be rotatable about a longitudinal axis; an optical element provided in the insertion portion to tilt an optical axis in a direction offset from the longitudinal axis direction; a robotic arm that moves and holds the endoscope such that the endoscope is rotatable about the longitudinal axis; and at least one processor comprising hardware, wherein the processor is configured to: transmit, to the robotic arm, a first signal for moving the endoscope in the longitudinal axis direction, detect a first moving direction of an object within first two images by using the first two images captured by the imaging sensor before and after the transmission of the first signal, estimate a first amount of rotation of the optical element around the longitudinal axis with respect to the imaging sensor based on the first movement direction, transmit, to the moving device, a second signal for moving the endoscope perpendicular to the longitudinal axis direction, detect a second moving direction of the object within second two images by using the second two images captured by the imaging sensor before and after the transmission of the second signal, and estimate a second amount of rotation about the longitudinal axis between the robotic arm and the endoscope based on the second moving direction and the first amount of rotation.

According to another aspect of the present disclosure, there is provided an endoscope movement control method for controlling a robotic arm for moving an endoscope, the endoscope comprising an insertion portion extending in a longitudinal axis direction, an imaging sensor disposed at a proximal end of the insertion portion so as to be rotatable about a longitudinal axis, and an optical element that is provided in the insertion portion to tilt an optical axis in a direction offset from the longitudinal axis direction, and the robotic arm holding the endoscope such that the endoscope is rotatable about the longitudinal axis, the endoscope movement control method comprising: moving the endoscope in the longitudinal axis direction by the robotic arm; detecting a first moving direction of an object in first two images by using the first two images captured by the imaging sensor before and after the movement in the longitudinal axis direction; estimating a first amount of rotation of the optical element about the longitudinal axis with respect to the imaging sensor based on the first moving direction; moving the endoscope in a direction perpendicular to the longitudinal axis direction by the robotic arm; detecting a second moving direction of the object in second two images using two images captured by the imaging sensor before and after the movement in the direction perpendicular to the longitudinal axis direction; and estimating a second amount of rotation about the longitudinal axis between the robotic arm and the endoscope based on the second moving direction and the first amount of rotation.

According to another aspect of the present disclosure, there is provided a non-transitory computer-readable recording medium in which an endoscope movement control program for controlling a robotic arm for moving an endoscope is stored, the endoscope comprising an insertion portion extending in a longitudinal axis direction, an imaging sensor disposed at a proximal end of the insertion portion so as to be rotatable about a longitudinal axis, and an optical element that is provided in the insertion portion to incline an optical axis in a direction offset from the longitudinal axis direction, the robotic arm holding the endoscope such that the endoscope is rotatable about the longitudinal axis, and the endoscope movement control program causing a computer to: move the endoscope in the longitudinal axis direction by the robotic arm; detect a first moving direction of an object in first two images by using two images captured by the imaging sensor before and after the movement in the longitudinal axis direction; estimate a first amount of rotation of the optical element about the longitudinal axis with respect to the imaging sensor based on the first moving direction; move the endoscope in a direction perpendicular to the longitudinal axis direction by the robotic arm; detect a second moving direction of the object in the second two images by using the second two images captured by the imaging sensor before and after the movement in the direction perpendicular to the longitudinal axis direction; and estimate a second amount of rotation about the longitudinal axis between the robotic arm and the endoscope based on the second moving direction and the first amount of rotation.

DESCRIPTION OF EMBODIMENTS

First Embodiment

An endoscope system 1, an endoscope movement control device 5, a method, a program, and a recording medium according to a first embodiment of the present disclosure will be described with reference to the drawings.

Figure 1:
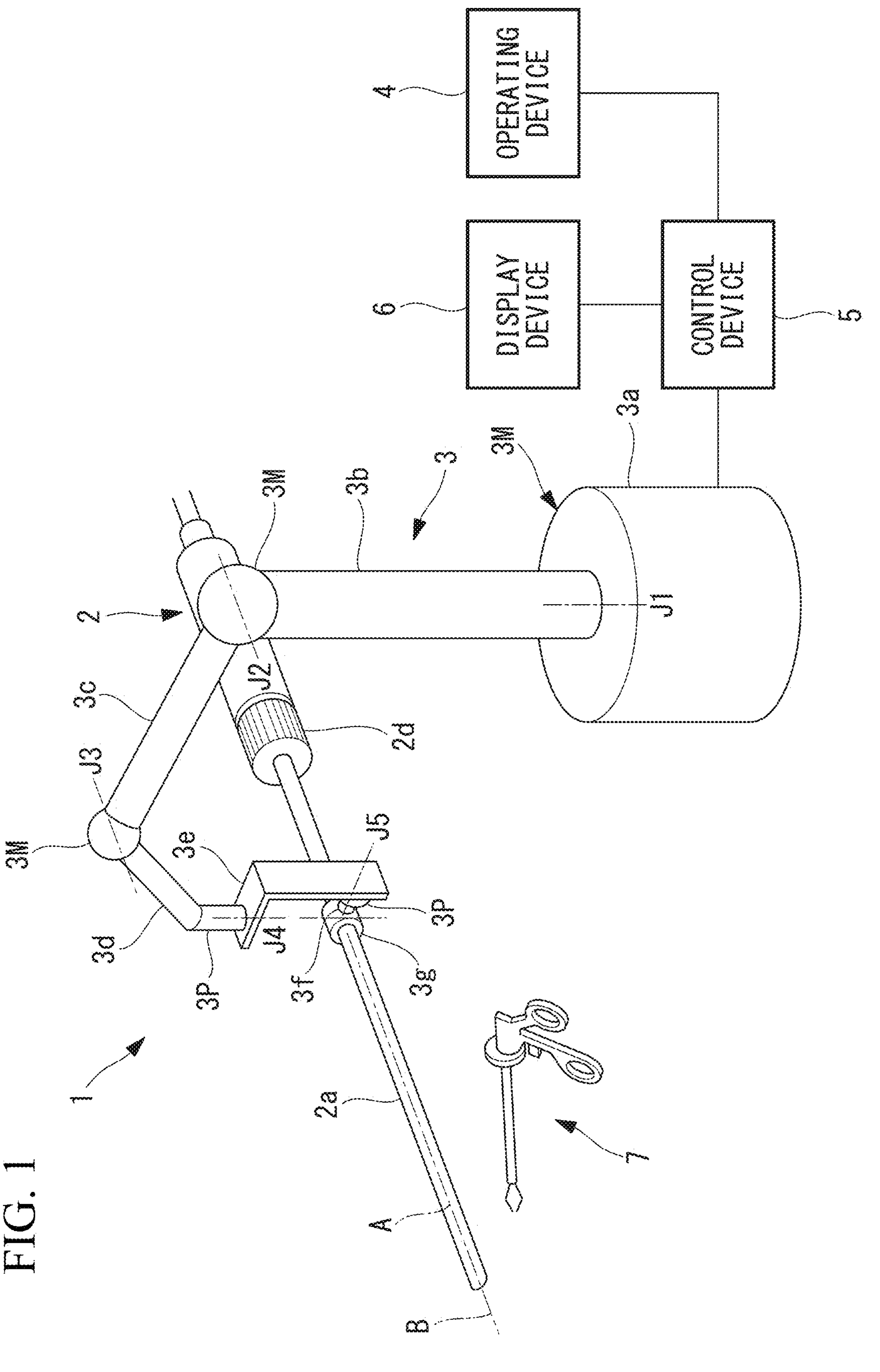
FIG. 1 is an overall configuration diagram of an endoscope system according to a first embodiment of the present disclosure.

As shown in FIG. 1, the endoscope system 1 according to the present embodiment includes an endoscope 2, a moving device 3 for holding and moving the endoscope 2, an operating device 4 to be operated by a user, a control device (endoscope movement control device) 5 for controlling the moving device 3 based on an operation signal from the operating device 4, and a display device 6.

The endoscope 2 is a rigid endoscope including an elongated and rigid lens tube portion (insertion portion) 2*a*, an optical system (optical element) 2*b* disposed in the lens tube portion 2*a*, and a camera head 2*c* disposed at a base end of the lens tube portion 2*a*. Furthermore, the endoscope 2 is an oblique-viewing type endoscope 2 having a visual axis (optical axis) B which is tilted at a predetermined angle by an optical system 2*b* with respect to a longitudinal axis A extending along the center in the radial direction of the lens tube portion 2*a*.

The lens tube portion 2*a* is attached to the camera head 2*c* so as to be rotatable around the longitudinal axis A. An operation ring 2*d* is fixed to the lens tube portion 2*a*. An operator can rotate the lens tube portion 2*a* around the longitudinal axis A with respect to the camera head 2*c* by rotating the operation ring 2*d* around the longitudinal axis A while holding the camera head 2*c*. Alternatively, the operator can also rotate the lens tube portion 2*a* around the longitudinal axis A with respect to the camera head 2*c* by rotating the camera head 2*c* around the longitudinal axis A while holding the operation ring 2*d*.

An imaging element 2*e* for imaging light focused by the optical system 2*b* is fixed inside the camera head 2*c*. The imaging element 2*e* includes an imaging surface which is arranged perpendicularly to the longitudinal axis A such that the longitudinal axis A passes through the center thereof. The imaging element 2*e* is an image sensor such as a CCD (Charge Coupled Device) image sensor or a CMOS (Complementary Metal Oxide Semiconductor) image sensor.

Figure 3:
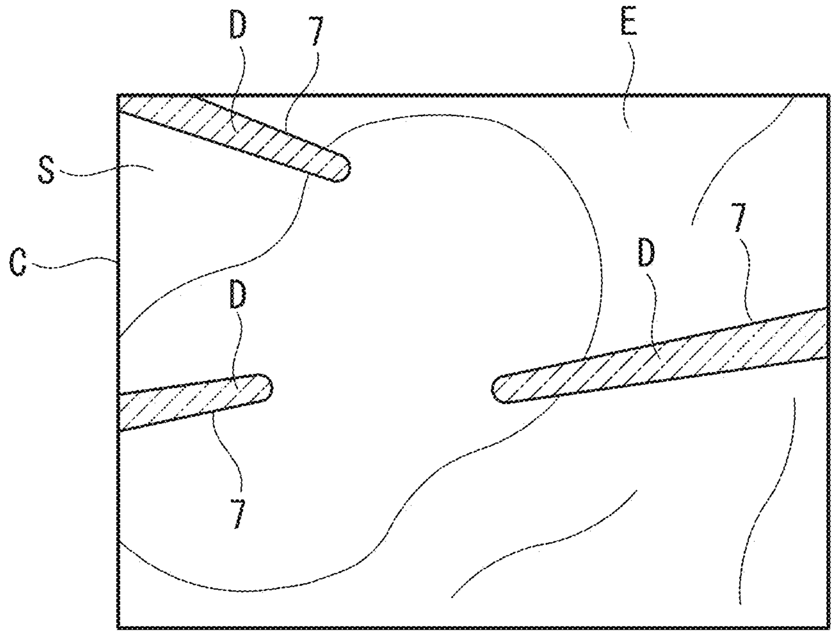
FIG. 3 is a diagram showing an example of a treatment tool area and other areas in an endoscopic image.

The endoscope 2 is inserted into a body together with one or more treatment tools 7, and an endoscopic image (image) C including the one or more treatment tools 7 (see FIG. 3) is captured by the imaging element 2*e*, and transmitted through the control device 5 to the display device 6. The display device 6 is any display such as a liquid crystal display or an organic EL display. The operator manipulates the treatment tools 7 while observing the endoscopic image C displayed on the display device 6.

The moving device 3 is a five-degree-of-freedom robot arm having a plurality of, for example, three driving joints (joints) 3M and two passive joints 3P. The moving device 3 includes, for example, a base 3*a* installed on a horizontal plane, and a first link 3*b* to be rotationally driven with respect to the base 3*a* around a vertical first axial line J1. Further, the moving device 3 includes a second link 3*c* to be rotationally driven with respect to the first link 3*b* around a horizontal second axial line J2, and a third link 3*d* to be rotationally driven with respect to the second link 3*c* around a horizontal third axial line J3. Further, the moving device 3 includes a fourth link 3*e* that is supported to be freely rotatable with respect to the third link 3*d* about a fourth axial line J4 extending along a plane that is orthogonal to the third axial line J3 and contains the first axial line J1, and a fifth link 3*f* which is supported to be rotatable with respect to the fourth link 3*e* around a fifth axial line J5 perpendicular to the fourth axial line J4.

The moving device 3 includes a holder 3*g* that is provided at the distal end of the fifth link 3*f* and holds the lens tube portion 2*a* of the endoscope 2 so as to make the lens tube portion 2*a* rotatable around the longitudinal axis A. The holder 3*g* holds the lens tube portion 2*a* such that the longitudinal axis A of the lens tube portion 2*a* passes through the intersection point between the fourth axial line J4 and the fifth axial line J5 and is perpendicular to the fifth axial line J5. The moving device 3 has five-degree-of-freedom. However, since the holder 3*g* holds the lens tube portion 2*a* so as to make the lens tube portion 2*a* rotatable around the longitudinal axis A, the moving device 3 has six-degree-of-freedom as a whole, so that the endoscope 2 can be arranged in a desired posture and at a desired position.

The endoscope 2 is moved by an interlocking operation of the three driving joints 3M and the two passive joints 3P of the moving device 3, whereby the position and posture of the endoscope 2 are three-dimensionally changed.

Figure 4:
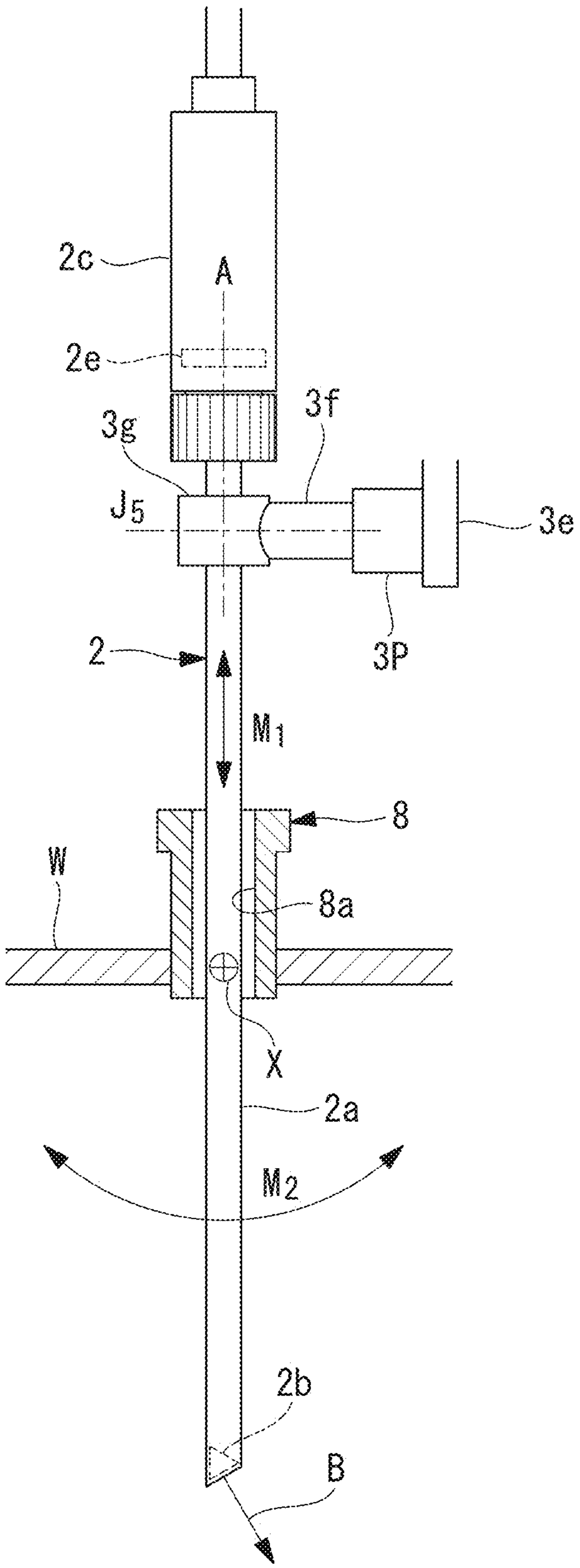
FIG. 4 is a partial longitudinal sectional view showing the endoscope and a trocar of the endoscope system of FIG. 1.

When using the endoscope 2, as shown in FIG. 4, the lens tube portion 2*a* of the endoscope 2 is inserted into a through-hole 8*a* of a trocar 8 that has been attached to an abdominal wall W of a patient by penetrating the trocar 8 through the abdominal wall W, thereby observing the inside of the patient's abdominal cavity. The trocar 8 is swingable about a pivot point X near the abdominal wall W, and the inner diameter of the through-hole 8*a* is set to be slightly larger than the outer diameter of the lens tube portion 2*a*. The gap between the through-hole 8*a* and the lens tube portion 2*a* is hermetically sealed by a sealing member made of an elastic material (not shown).

The three-dimensional position of the distal end of the third link 3*d* is uniquely determined by driving the three driving joints 3M. The moving direction of the endoscope 2 is restricted by the trocar 8. Therefore, when the distal end position of the third link 3*d* is changed, the endoscope 2 swings the trocar 8 around the pivot point X or move the lens tube portion 2*a* in the longitudinal axis direction A inside the through-hole 8*a* of the trocar 8, and passively rotates the two passive joints 3P so as to follow the above movement. The rotation of the lens tube portion 2*a* around the longitudinal axis A relative to the holder 3*g* is maintained in a state manually adjusted by the operator.

Each of the three driving joints 3M of the moving device 3 is equipped with an angle sensor 3*h* for detecting the rotation angle thereof. The angle sensor 3*h* is, for example, an encoder, a potentiometer, or a Hall sensor provided at each driving joint 3M.

The operating device 4 has a user interface 4*a* including input devices such as keys, a joystick, buttons, and a touch panel. The operator can input an instruction for moving the endoscope 2 to the operating device 4 by operating the user interface 4*a*. The operating device 4 transmits an operating signal based on an operation of the user interface 4*a* to the control device 5.

Further, the user interface 4*a* can accept a trigger input from the operator. As described later, the trigger is used for executing processing of estimating the amounts of rotation amounts β and θ of the endoscope 2.

Figure 2:
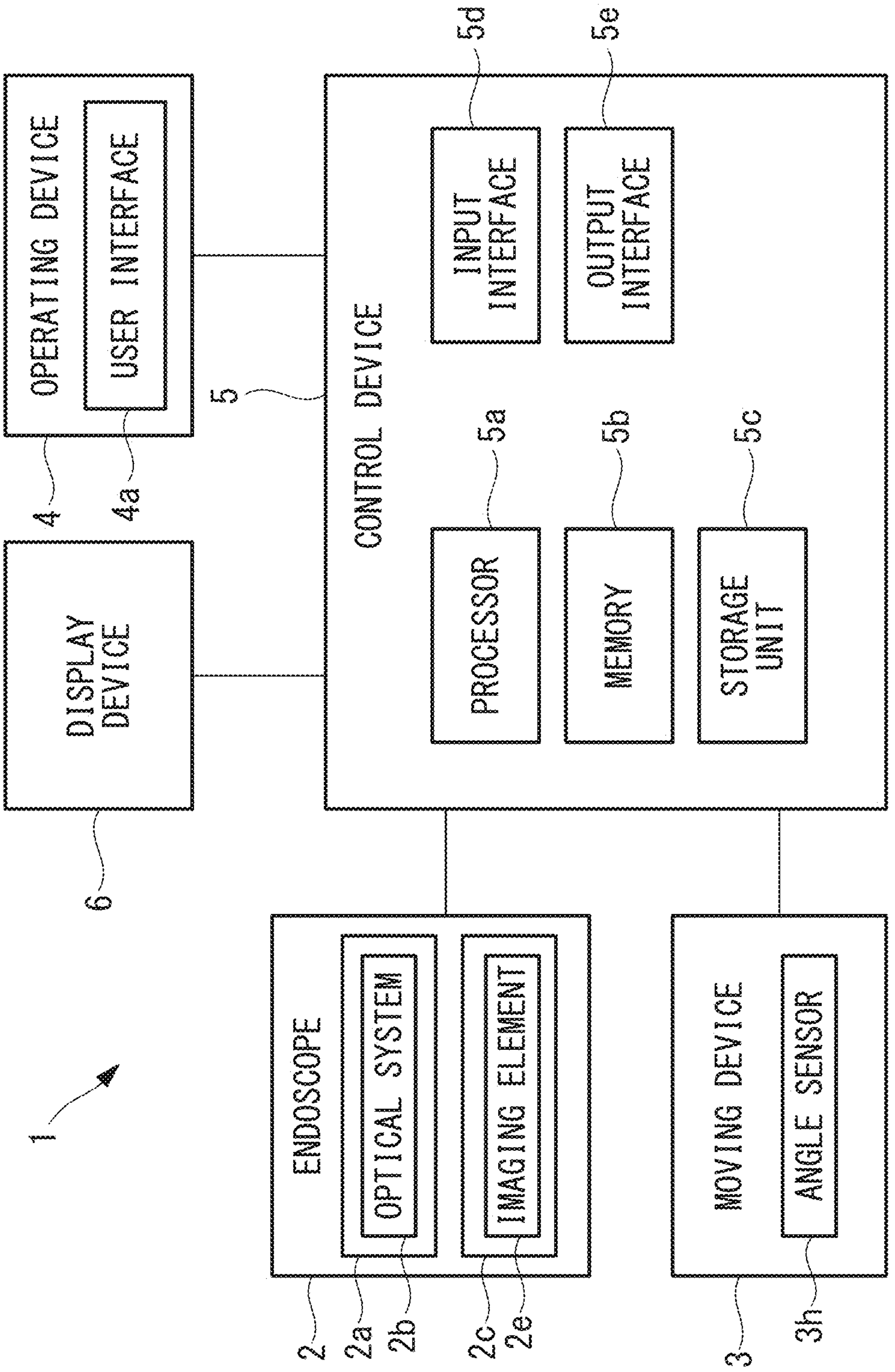
FIG. 2 is a block diagram showing the overall configuration of the endoscope system in FIG. 1.

As shown in FIG. 2, the control device 5 includes at least one processor 5*a*, a memory 5*b*, a storage unit 5*c*, an input interface 5*d*, and an output interface 5*e*.

The control device 5 is connected to the surrounding endoscope 2, moving device 3 (robotic arm), operating device 4, and display device 6 via the input interface 5*d* and the output interface 5*e*, and transmits and receives an endoscopic image C, information on the rotation angle of the driving joints 3M, signals, etc. via the interfaces 5*d* and 5*e*.

The memory 5*b* is, for example, a semiconductor memory including ROM (read-only memory) or RAM (random access memory) area.

The storage unit 5*c* is a computer-readable non-transitory recording medium, and is, for example, a nonvolatile recording medium including a hard disk or a semiconductor memory such as a flash memory.

The processor 5*a* controls the moving device 3 based on the operation signal from the operating device 4, thereby moving the endoscope 2 according to an instruction input to the user interface 4*a* by the operator.

Here, the operator can rotate the endoscope 2 around the longitudinal axis A according to two ways by operating the endoscope 2 attached to the holder 3*g*. First, the lens tube portion 2*a* is rotated around the longitudinal axis A with respect to the camera head 2*c* by manipulating the operation ring 2*d*, which makes it possible to change the relative angle (first amount of rotation) β between the camera head 2*c* and the lens tube portion 2*a*. Second, the lens tube portion 2*a* is rotated around the longitudinal axis A with respect to the holder 3*g*, which makes it possible to change the angle (second amount of rotation) θ representing the direction of the visual axis B of the lens tube portion 2*a* with respect to the holder 3*g*.

In order for the operator to attach the endoscope 2 to the moving device 3 and intuitively move the endoscope 2 vertically and horizontally while watching the endoscopic image C displayed on the display device 6, it is necessary that the amounts of rotation β and θ between the moving device 3 and the endoscope 2 have been grasped.

In the endoscope system 1 according to the present embodiment, the processor 5*a* estimates the amounts of rotation β and θ of the endoscope 2 by executing a program (endoscope movement control program) which is recorded in the storage unit 5*c* and read out to the memory 5*b*.

Hereinafter, an endoscope movement control method by the endoscope system 1 according to the present embodiment will be described with reference to the drawings.

The processing of estimating the amounts of rotation β and θ of the endoscope 2 is started by the operator inputting a trigger to the user interface 4*a*.

Figure 5A:
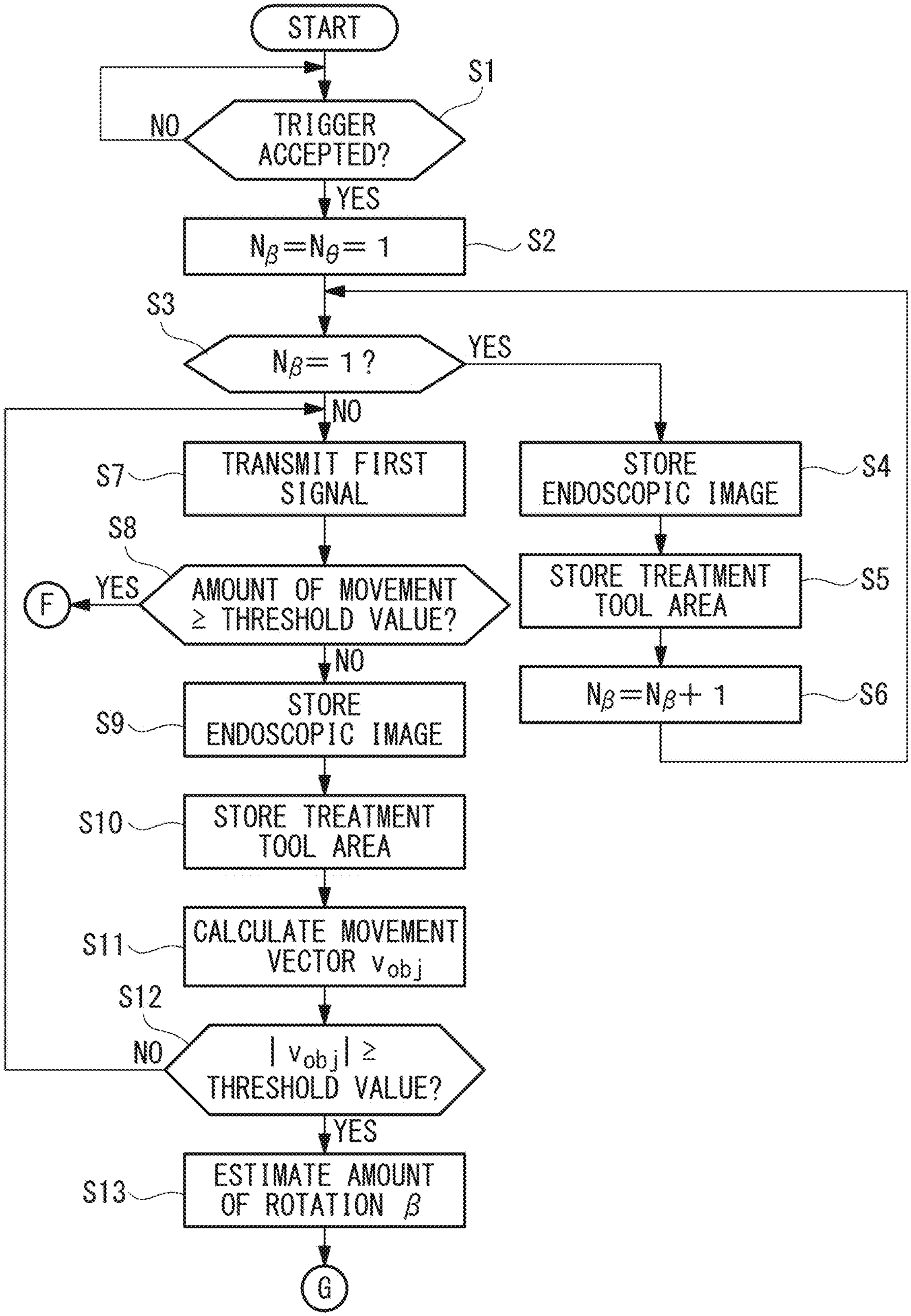
FIG. 5A is a flowchart illustrating an endoscope movement control method by the endoscope system of FIG. 1.

As shown in FIG. 5A, the processor 5*a* first determines whether a trigger has been received (step S1), and if accepted, the processor 5*a* initializes the numbers of loops NB and $N_\theta$, respectively (step S2). Next, the processor 5*a* determines whether $N_\beta=1$ is satisfied (step S3), and if $N_\beta=1$ is satisfied, the processor 5*a* stores a first endoscopic image C acquired by the endoscope 2 at that time into the memory 5*b* (step S4). Further, the processor 5*a* recognizes treatment tools (moving objects) 7 in the first endoscopic image C by using a known method such as image recognition using artificial intelligence, and stores areas of the treatment tools 7 as treatment tool areas D into the memory 5*b* (step S5). Then, the processor 5*a* increments the number of loops $N_\beta$ (step S6), and repeats the processing from step S3.

If the processor 5*a* determines in step S3 that $N_\beta\neq1$ is satisfied, the processor 5*a* transmits a first signal for activating the moving device 3 so as to move the endoscope 2 in one direction along the longitudinal axis A (Step S7). It is determined whether the amount of movement of the endoscope 2 caused by the moving device 3 being activated with the first signal is equal to or more than a predetermined threshold value (step S8). If it is equal to or more than the threshold value, the processing is terminated.

When determining that the amount of movement of the endoscope 2 is smaller than the threshold value, the processor 5*a* stores a second endoscopic image C acquired by the endoscope 2 at that time into the memory 5*b* (step S9). Further, the processor 5*a* recognizes the treatment tools (moving objects) 7 in the second endoscopic image C, and stores the areas of the treatment tools 7 as treatment tool areas D into the memory 5*b* (step S10).

Figure 6:
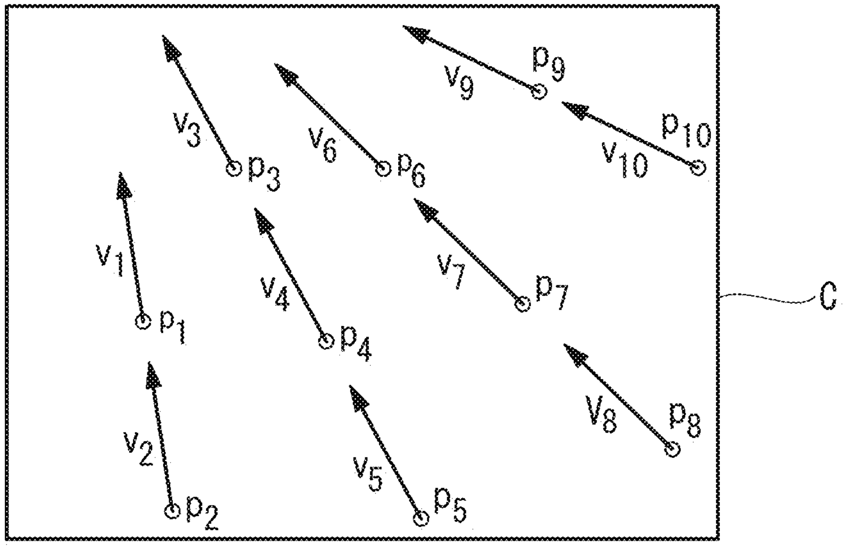
FIG. 6 is a diagram showing an example of a movement vector calculated from an endoscopic image.

A first moving direction $M_1$ of an object S in the endoscopic image C is detected using the first endoscopic image C and the second endoscopic image C (step S11). Specifically, the processor 5*a* uses a known method such as optical flow to estimate a movement vector $v_{obj}$ of the object S in another area E obtained by excluding the treatment tool areas D from the two endoscopic images C captured before and after the endoscope 2 is moved by the moving device 3. As shown in FIG. 6, the movement vector $v_{obj}$ is a two-dimensional vector that indicates the moving direction of each of a plurality of different feature points in the other area E within the endoscopic image C.

Next, the processor 5*a* determines whether the magnitude of the estimated movement vector $v_{obj}$ is equal to or more than a threshold value (step S12). The determination of the magnitude of the movement vector $v_{obj}$ is performed using the magnitude of any of estimated movement vectors $v_{obj}$ or the average value of the magnitudes of the estimated movement vectors $v_{obj}$.

When the magnitude of the movement vector $v_{obj}$ is smaller than the threshold value, the processor 5*a* repeats the processing from step S7. When the magnitude of the movement vector $v_{obj}$ is equal to or more than the threshold value, the processor 5*a* estimates the amount of rotation β of the endoscope 2 from the estimated movement vector $v_{obj}$ (step S13).

The estimation of the amount of rotation β of the endoscope 2 is performed as follows.

Figure 7:
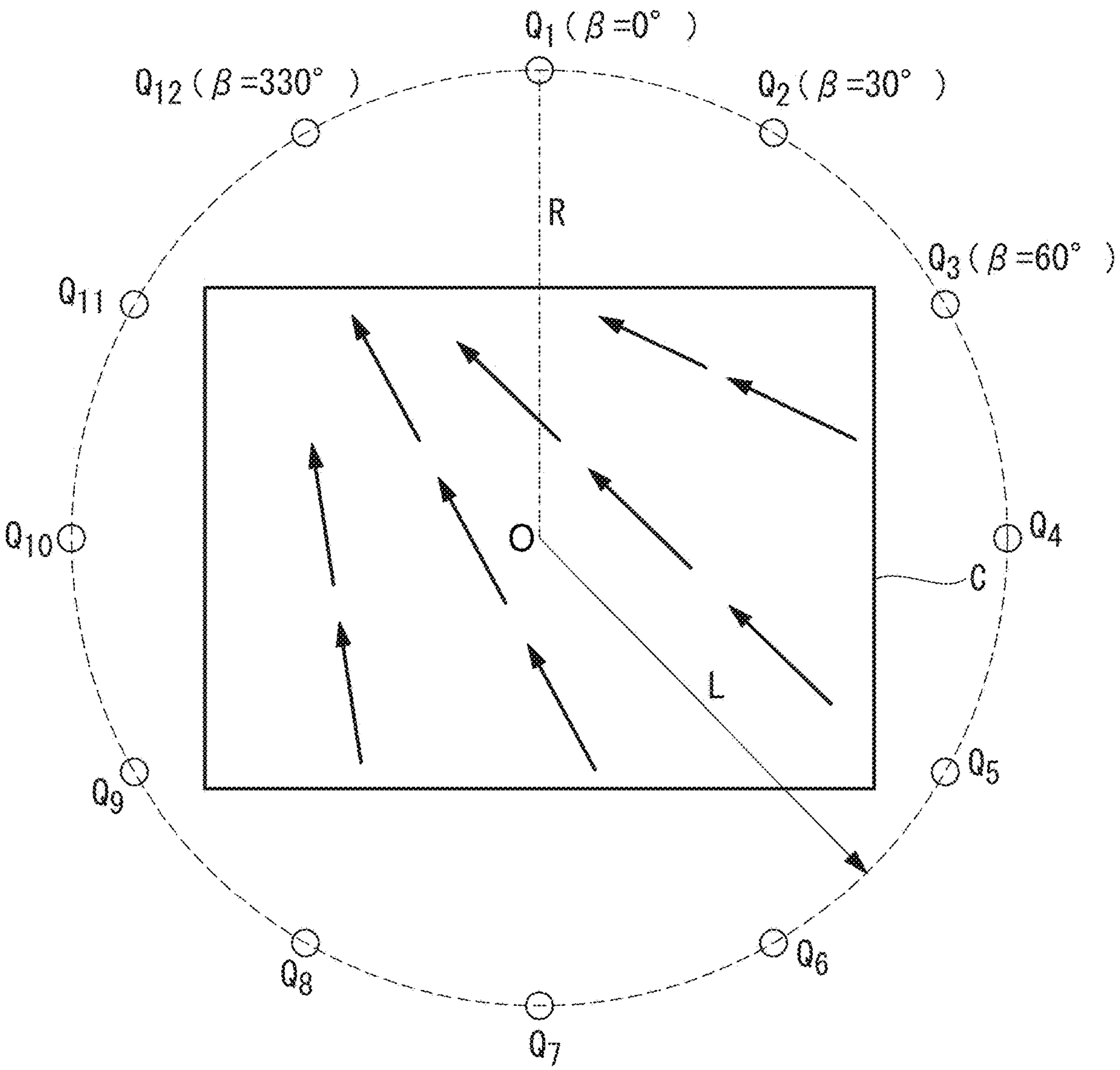
FIG. 7 is a diagram showing an example of a temporary vanishing point set in the endoscopic image.

First, the processor 5*a* calculates the intersection point (hereinafter also referred to as a vanishing point) of straight lines along the directions of a plurality of movement vectors $v_{obj}$ estimated for a plurality of feature points on the endoscopic image C. Specifically, as shown in FIG. 7, the processor 5*a* arranges a plurality of temporary vanishing points $Q_1$ to $Q_{12}$ at equal intervals on a circumference of a radius L from the center O (hereinafter referred to as an image center) of the endoscopic image C, and stores the respective positions of the temporary vanishing points $Q_1$ to $Q_{12}$. FIG. 7 shows an example in which the vanishing points $Q_1$ to $Q_{12}$ are arranged at intervals of 30°.

The radius L is the distance from the image center O to the vanishing point, and can be calculated using Formula (1).

[Formula 1]

$$L = \left(\frac{H \cdot \tan(\alpha)}{2 \cdot \tan(\psi/2)}\right) \tag{1}$$

Figure 8:
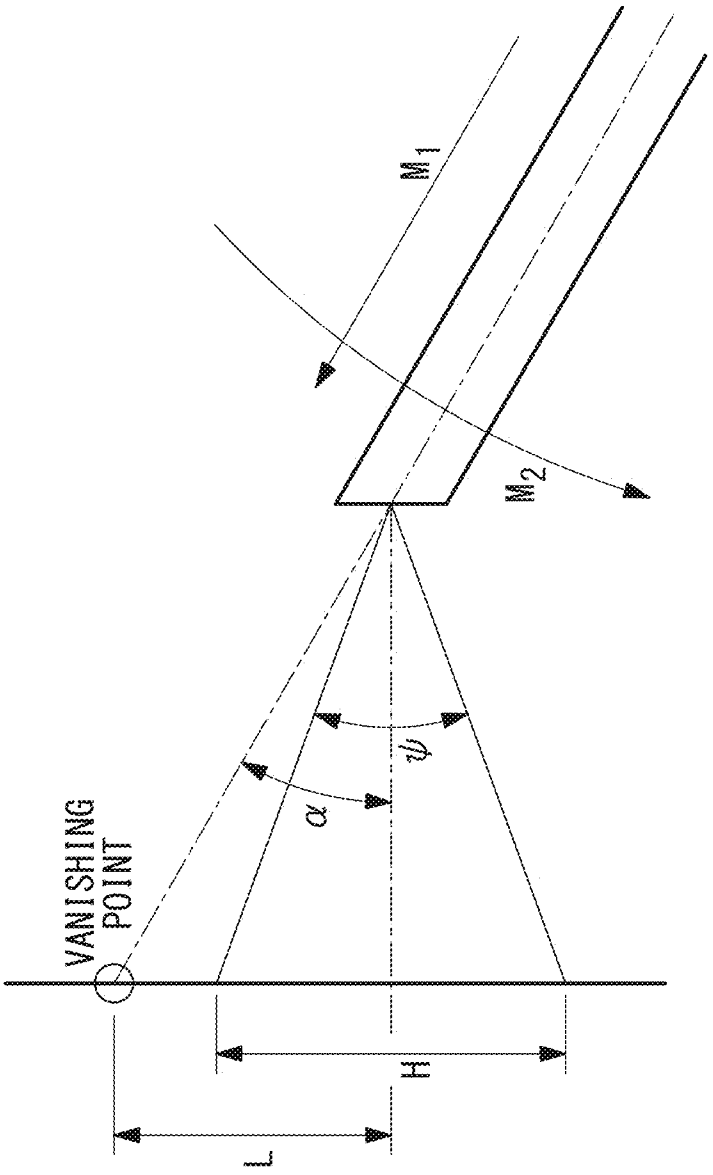
FIG. 8 is a diagram showing the relation between a viewing angle and the vanishing point of the endoscope.

Here, as shown in FIG. 8, H represents the height (pixel) of the endoscopic image C, α represents the angle of the visual axis B with respect to the longitudinal axis A of the endoscope 2, and φ represents the field of view of the endoscope 2. For example, the angle α may be 30 degrees.

The processor 5*a* uses, as a reference line R, a straight line which connects the position of a vanishing point $Q_1$ for the amount of rotation β=0° and the image center O, and sets the temporary vanishing points $Q_1$ to $Q_{12}$, for example, at intersection points between the circle of the radius L and straight lines obtained by rotating the reference line R by every 30° around the image center O. As a result, for example, when the temporary vanishing point $Q_2$ at a position where rotation of 30° is performed with respect to the reference line R is selected as the vanishing point, the amount of rotation β of the endoscope 2 can be estimated to be β=30°.

Figure 9:
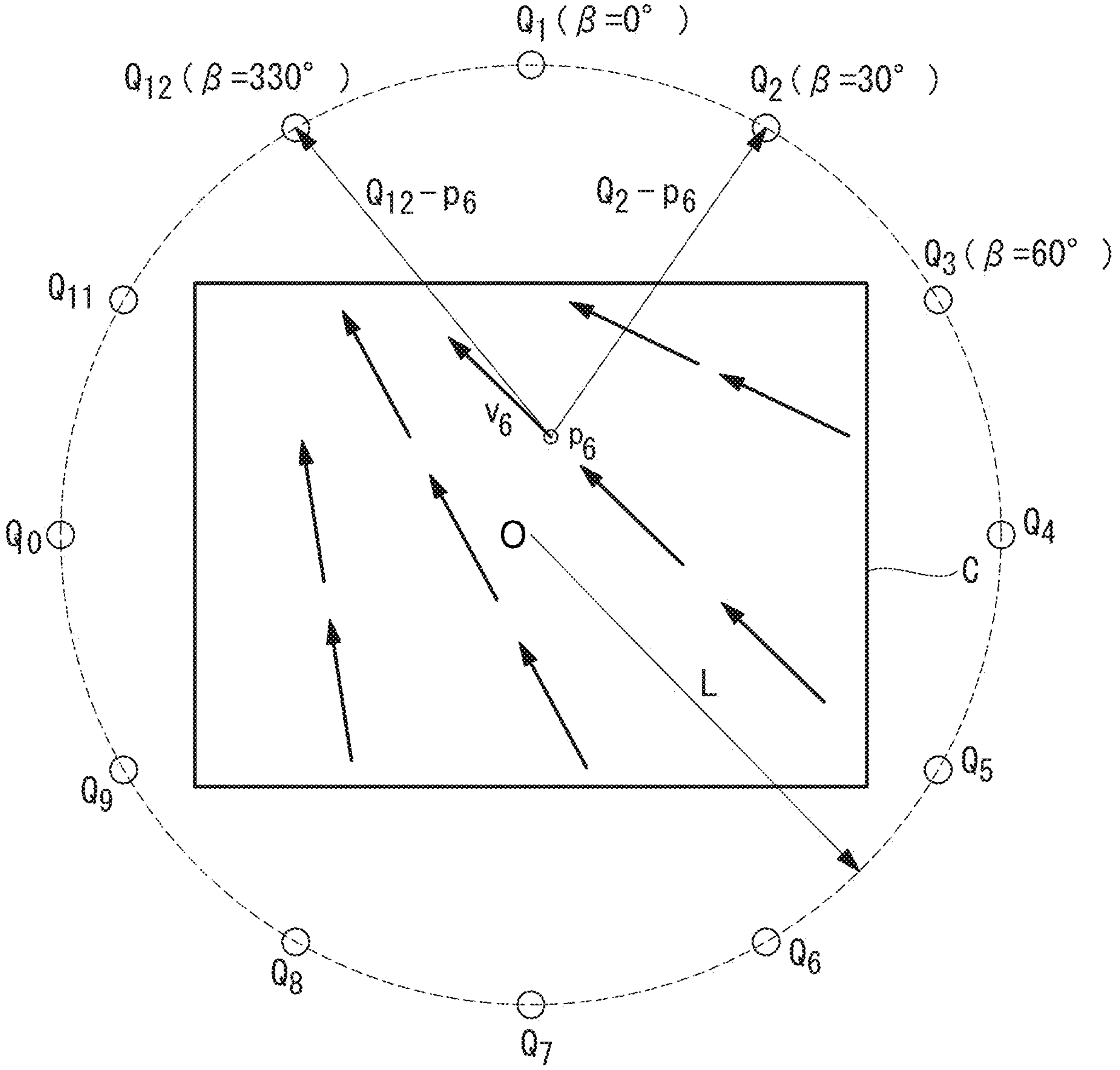
FIG. 9 is a diagram illustrating processing for determining a vanishing point from the temporary vanishing point set in FIG. 7.

The processor 5*a* calculates, for each temporary vanishing point $Q_j$, the inner product of each movement vector $v_i$ and a vector $(Q_j-p_i)$ connecting the origin $p_i$ of each movement vector $v_i$ and the temporary vanishing point $Q_j$. FIG. 9 illustrates a vector $(Q_2-p_6)$ connecting the temporary vanishing point $Q_2$ and the origin $p_6$ of the vector $v_6$ and a vector $(Q_{12}-p_6)$ connecting the temporary vanishing point $Q_{12}$ and the origin $p_6$ of the vector $v_6$. Then, for example, as shown in Formula (2), the processor calculates the sum of inner products for all movement vectors $v_i$ as an evaluation function $U_j$, and selects, as the vanishing point, a temporary vanishing point $Q_j$ where the evaluation function $U_j$ is minimized.

[Formula 2]

$$U_j = \sum_{i=1}^{N} (Q_j - p_i) \cdot v_i \tag{2}$$

In the example shown in FIG. 9, the temporary vanishing point $Q_{12}$ is selected as the vanishing point.

As a result, the processor 5*a* estimates the rotation angle corresponding to the selected vanishing point, 330° in the example shown in FIG. 9, as the amount of rotation β of the endoscope 2.

Figure 5B:
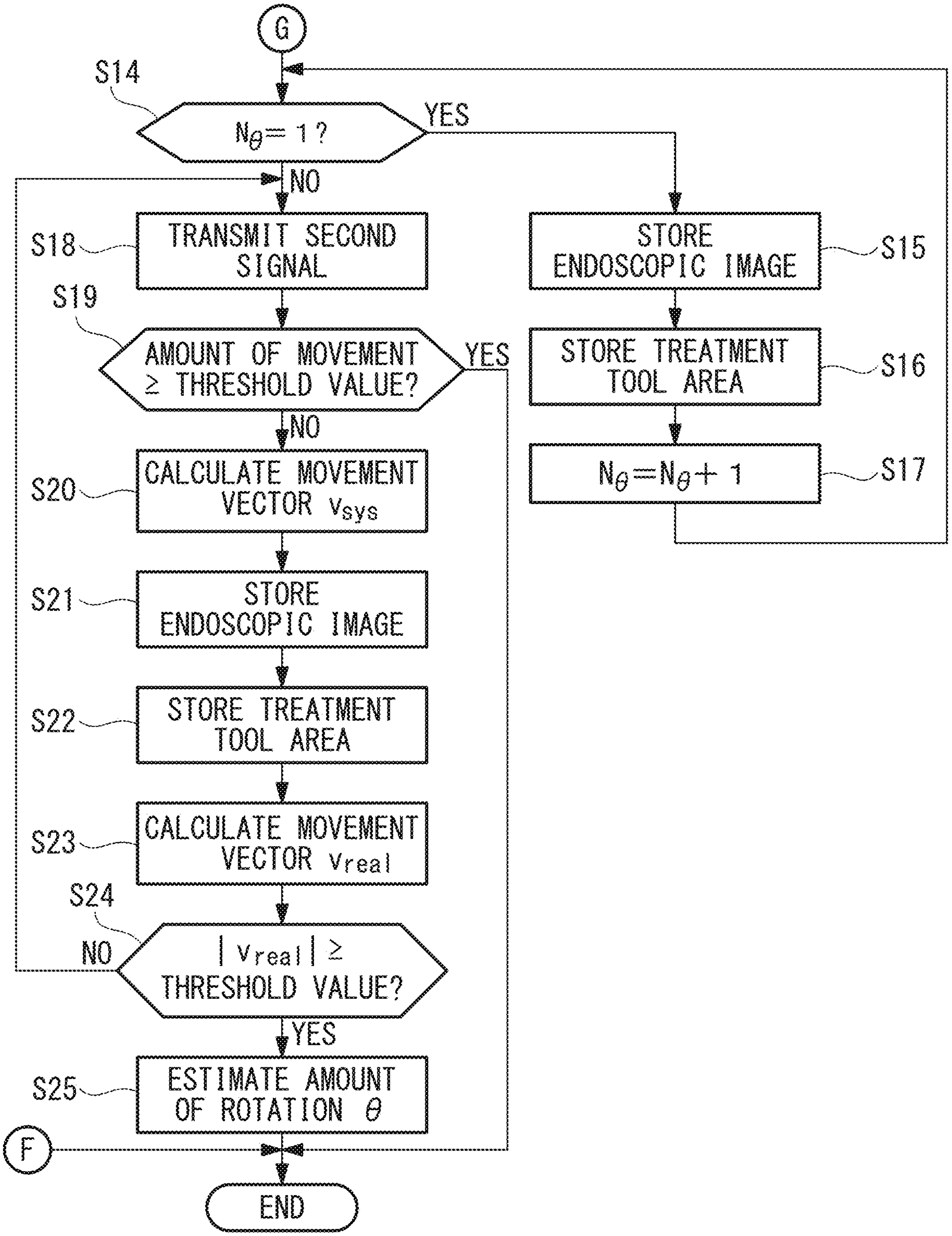
FIG. 5B is a flowchart following FIG. 5A.

Next, as shown in FIG. 5B, the processor 5*a* determines whether the number of loops $N_\theta$ satisfies $N_\theta=1$ (step S14). In case of $N_\theta=1$, the third endoscopic image C captured by the endoscope 2 at that time is stored in the memory 5*b* (step S15). Further, the processor 5*a* stores the areas of the treatment tools (moving objects) 7 in the third endoscopic image C as the treatment tool areas D in the memory 5*b* in the same manner as in step S5 (step S16). Then, the processor 5*a* increments the number of loops Ne (step S17), and repeats the processing from step S14.

In step S14, when determining that Nθ≠1 is satisfied, the processor 5*a* transmits a second signal for causing the moving device 3 to operate so as to move the endoscope 2 in one direction perpendicular to the longitudinal axis A (step S18). The processor 5*a* determines whether the amount of movement of the endoscope 2 caused by the moving device 3 being activated with the second signal is equal to or more than a predetermined threshold value (step S19), and when it is equal to or more than the threshold value, the processor 5*a* terminates the rotation amount estimation processing.

Figure 10:
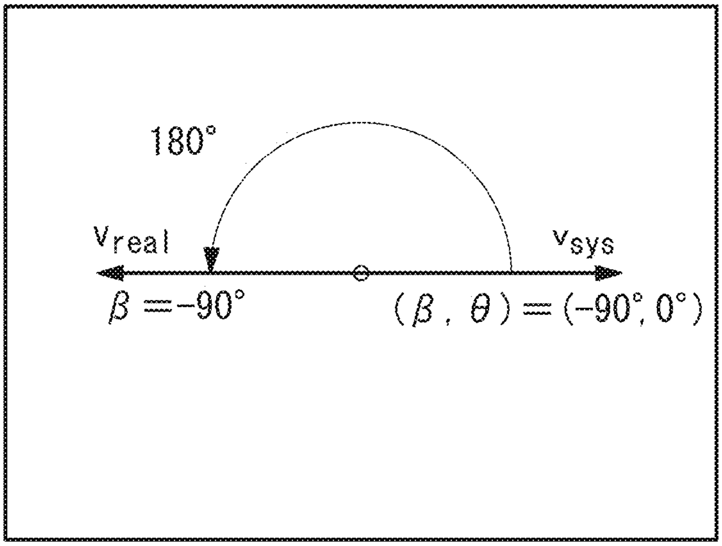
FIG. 10 is a diagram illustrating processing for determining an amount of rotation θ from a movement vector acquired from endoscopic images before and after movement in a direction perpendicular to a longitudinal axis of the endoscope.

When the movement amount of the endoscope 2 is smaller than the threshold value, the processor 5*a* uses the amount of rotation β estimated in step S13 to calculate a movement vector $v_{sys}$ of the object S in the endoscopic image C, which is assumed to be caused by transmission of the second signal when the amount of rotation θ is equal to a predetermined value, for example, 0° (step S20). FIG. 10 illustrates the movement vector $v_{sys}$ in case of (β, θ)=(−90°, 0°).

Then, the processor 5*a* stores, into the memory 5*b*, the fourth endoscopic image C captured after the endoscope 2 is moved with the second signal (step S21). Further, the processor 5*a* recognizes the treatment tools (moving objects) 7 in the fourth endoscopic image C, and stores the areas of the treatment tools 7 as the treatment tool areas D into the memory 5*b* (step S22).

The second moving direction $M_2$ of the object S in the endoscopic image C is detected using the third endoscopic image C and the fourth endoscopic image C (step S23). Specifically, the processor 5*a* uses a known method such as optical flow to estimate a movement vector $v_{real}$ of the object S in another area E obtained by excluding the treatment tool areas D from the two endoscopic images C captured before and after the endoscope 2 is moved by the moving device 3.

Next, the processor 5*a* determines whether the magnitude of the estimated movement vector $v_{real}$ is equal to or more than a threshold value (step S24). The determination of the magnitude of the movement vector $v_{real}$ is performed using the magnitude of any of estimated movement vectors $v_{real}$ or the average value of the magnitudes of the estimated movement vectors $v_{real}$.

When the magnitude of the movement vector $v_{real}$ is smaller than the threshold value, the processor 5*a* repeats the processing from step S18. When the magnitude of the movement vector $v_{real}$ is equal to or more than the threshold value, the processor 5*a* estimates the angle between the assumed movement vector $v_{sys}$ and the estimated movement vector $v_{real}$, which is 180° in the example shown in FIG. 10, as the amount of rotation θ of the endoscope 2 (step S25), and terminates the processing.

When the amounts of rotation β and θ of the endoscope 2 are estimated, the processor 5*a* uses the estimated amounts of rotation β and θ to correct a holder coordinate system Σr so that the holder coordinate system Σr and an endoscope coordinate system e match each other. The endoscope coordinate system Ce is a coordinate system fixed for the imaging element 2*e*, and the holder coordinate system Σr is a coordinate system fixed for the distal end of the holder 3*g*.

In one example, the endoscope coordinate system Ce is a rectangular coordinate system having Xe-axis, Ye-axis, and Ze-axis which are orthogonal to one another, and the holder coordinate system Σr is a rectangular coordinate system having Xr-axis, Yr-axis, and Zr-axis which are orthogonal to one another. The Xe-axis and the Xr-axis match the longitudinal axis A, the Ye-axis and the Yr-axis are parallel to the horizontal direction (left-right direction) of the endoscopic image C, and the Ze-axis and the Zr-axis are parallel to the vertical direction (up-and-down direction) of the endoscopic image C. The holder coordinate system Σr and the endoscope coordinate system Σe matching each other means that the directions of the Xe-axis and Xr-axis match each other, the directions of the Ye-axis and Yr-axis match each other, and the directions of the Ze-axis and Zr-axis match each other.

However, when the endoscope 2 is rotated by the amounts of rotation β and θ around the longitudinal axis A, a shift occurs between the endoscope coordinate system Ce and the holder coordinate system Σr. When the endoscope coordinate system Ce does not match the holder coordinate system Σr as described above, it is difficult for the operator who is observing the endoscopic image C displayed on the display device 6 to intuitively and accurately move the endoscope 2 in a desired direction by operating the user interface 4*a*.

The processor 5*a* makes the holder coordinate system Σr match the endoscope coordinate system Ce by correcting the holder coordinate system Σr based on the amounts of rotation β and θ. Specifically, the processor 5*a* corrects a DH (Denavit-Hartenberg) parameter of the moving device 3 based on the amounts of rotation β and @ so that the holder coordinate system Σr matches the endoscope coordinate system Ce.

The processor 5*a* controls the moving device 3 based on the corrected holder coordinate system Σr.

As described above, according to the present embodiment, the amounts of rotation β and θ which are manually adjusted by the operator are estimated, and the holder coordinate system Σr is corrected using the estimated amounts of rotation β and θ. Therefore, even in the case of the endoscope 2 consisting of an oblique-viewing endoscope, the operator can intuitively and accurately move the endoscope 2 in a desired direction by operating the user interface 4*a* while observing the endoscopic image C.

Furthermore, the amounts of rotation β and θ of the endoscope 2 can be calculated from the two endoscopic images C obtained before and after the moving device 3 is activated, respectively. In other words, it is not necessary to add any equipment such as a sensor to detect the amounts of rotation β and θ, and the amounts of rotation β and θ can be estimated without any sensor.

If a device such as a sensor for detecting the amounts of rotation β and θ of the endoscope 2 is added to the moving device 3, it would be possible to easily measure the amounts of rotation amounts β and θ. However, in this case, it is impossible to use any existing moving device 3, and it is necessary to improve the moving device 3. Moreover, the size and weight of the moving device 3 increase, and the moving device 3 may become an obstacle to the operator. Therefore, according to the present embodiment, there is no need to improve the moving device 3, and the moving device 3 can be easily miniaturized.

Further, according to the present embodiment, the area E other than the treatment tool areas D in the endoscopic image C is used for estimating the movement vector $v_{obj}$. As a result, even when a moving treatment tool 7 exists in the endoscopic image C, a highly accurate movement vector $v_{obj}$ that accurately represents the moving direction of the endoscope 2 can be estimated. The amounts of rotation β and θ of the endoscope 2 can be calculated based on such a highly accurate movement vector $v_{obj}$, and the holder coordinate system Σr can be accurately corrected. Furthermore, based on the accurately corrected holder coordinate system Σr, the endoscope 2 can be moved by the moving device 3 in a direction that exactly corresponds to a direction input into the operating device 4 by the operator.

(First Modification)

Figure 11:
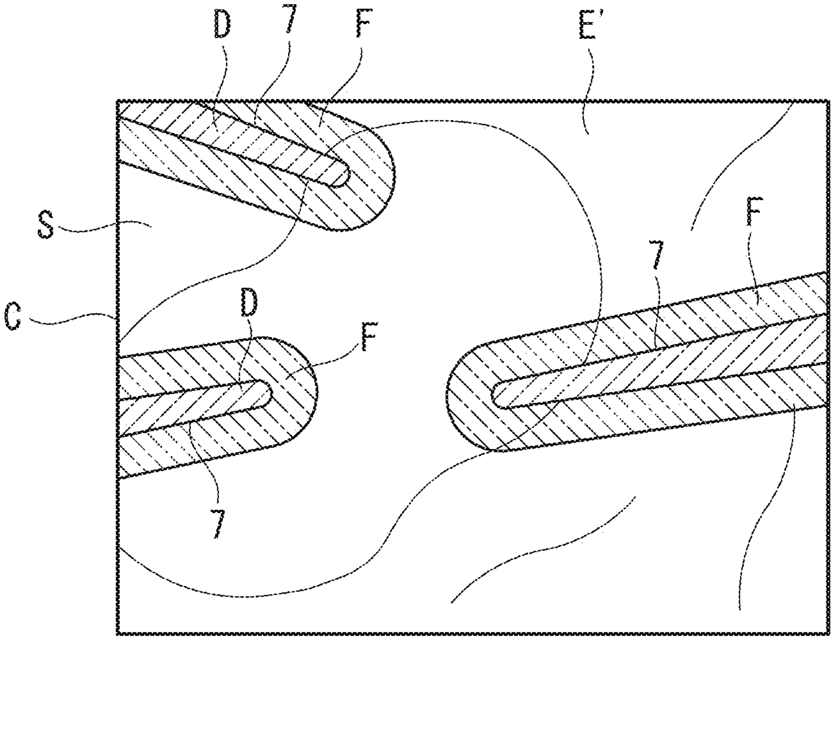
FIG. 11 is a diagram showing a first modification of the endoscope system shown in FIG. 1, and showing an example of a treatment tool area, a margin, and other areas in an endoscopic image.

In the present embodiment, as shown in FIG. 11, a treatment tool area estimator 51 may estimate the moving direction of the object S based on another area E' excluding areas obtained by adding margins F to the treatment tool areas D.

The margin F is an area that extends along the outline of the treatment tool area D and surrounds the treatment tool area D, and is, for example, a belt-shaped area having a predetermined width.

In the vicinity of the treatment tool 7, the movement of the object S may be affected by the movement of the treatment tool 7. For example, the object S may partially move in the vicinity of the treatment tool 7 due to the object S being pushed or pulled by the treatment tool 7.

By excluding the area obtained by adding the margin F to the treatment tool area D, it is possible to improve the estimation accuracy of the movement vectors $v_{obj}$ and $v_{real}$ Of the object S and more accurately estimate the amounts of rotation β and θ of the endoscope 2.

(Second Modification)

Further, in the present embodiment, a plurality of temporary vanishing points $Q_j$ corresponding to the amount of rotation β is set, and the vanishing point is selected using the evaluation function $U_j$ shown in Formula 2. In this case, the temporary vanishing points are set at every 30°, but they may be set at every smaller angles. As a result, the amount of rotation β can be estimated with higher accuracy.

(Third Modification)

Figure 12:
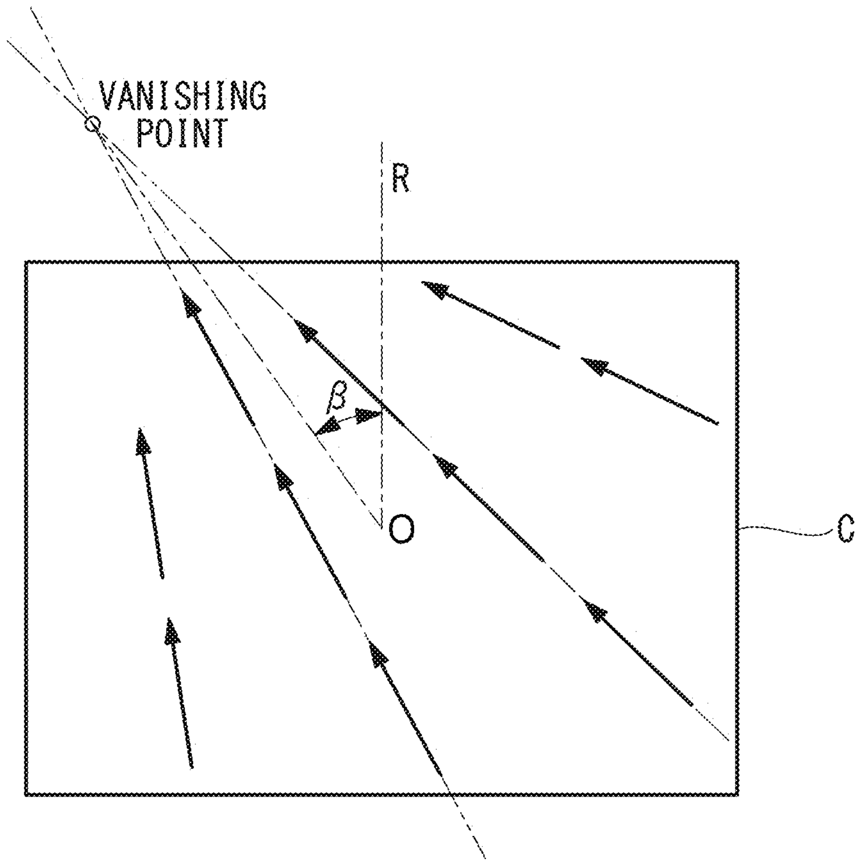
FIG. 12 is a diagram illustrating a third modification of the endoscope system in FIG. 1, and illustrating processing for determining a vanishing point from a movement vector in FIG. 6.

Further, instead of setting a plurality of temporary vanishing points $Q_j$ corresponding to the amount of rotation β, functions of a plurality of straight lines along movement vectors $v_{obj}$ of a plurality of feature points in the endoscopic image C are determined, and as shown in FIG. 12, the intersection of these straight lines may be calculated as the vanishing point. Then, the angle of a straight line connecting the calculated intersection point and the image center O with respect to the reference line R may be calculated as the amount of rotation β. As a result, the amount of rotation β can be estimated with higher accuracy.

(Fourth Modification)

Further, as described above, a gap exists in the radial direction between the lens tube portion 2*a* of the endoscope 2 and the through-hole 8*a* of the trocar 8. When the moving device 3 has the passive joint 3P, there may occur a situation that even if an attempt is made to move the lens tube portion 2*a* in the longitudinal axis direction A, the lens tube portion 2*a* shifts in a direction intersecting the longitudinal axis A by the amount corresponding to the gap. The optical flow when the lens tube portion 2*a* is moved in the longitudinal axis direction A is used in order to estimate the amount of rotation β. Therefore, if the lens tube portion 2*a* shifts in the direction intersecting the longitudinal axis A, the accuracy of estimating the vanishing point and thus the amount of rotation β deteriorates.

Therefore, the lens tube portion 2*a* is moved in the longitudinal axis direction A sufficiently larger than the gap between the lens tube portion 2*a* and the trocar 8 (for example, 20 mm or more when the gap is 2 to 3 mm). As a result, it is possible to reduce the ratio of the deviation amount of the movement vector $v_{obj}$ caused by the gap, so that the estimation accuracy of the amount of rotation β can be improved.

(Fifth Modification)

Further, in order to accurately arrange the lens tube portion 2*a* of the endoscope 2 at a desired position and in a desired posture, a moving device 3 having six-degree-of-freedom may required. The moving device 3 in general as a robotic arm that can have 6 degrees of freedom, however, a moving device having 3 degrees of freedom or more can be used. In the present embodiment, as described above, the six-degree-of-freedom holder 3*g* holds the endoscope 2 so that the endoscope 2 is manually rotatable around the longitudinal axis A. For this reason, for example, some posture of the endoscope 2 may cause the entire endoscope 2 to rotate around the longitudinal axis A when the lens tube portion 2*a* of the endoscope 2 is moved in a direction perpendicular to the longitudinal axis A. In this case, the endoscopic images C obtained before and after the movement rotates, which makes it difficult to correctly calculate the moving direction of the object S.

Figure 13:
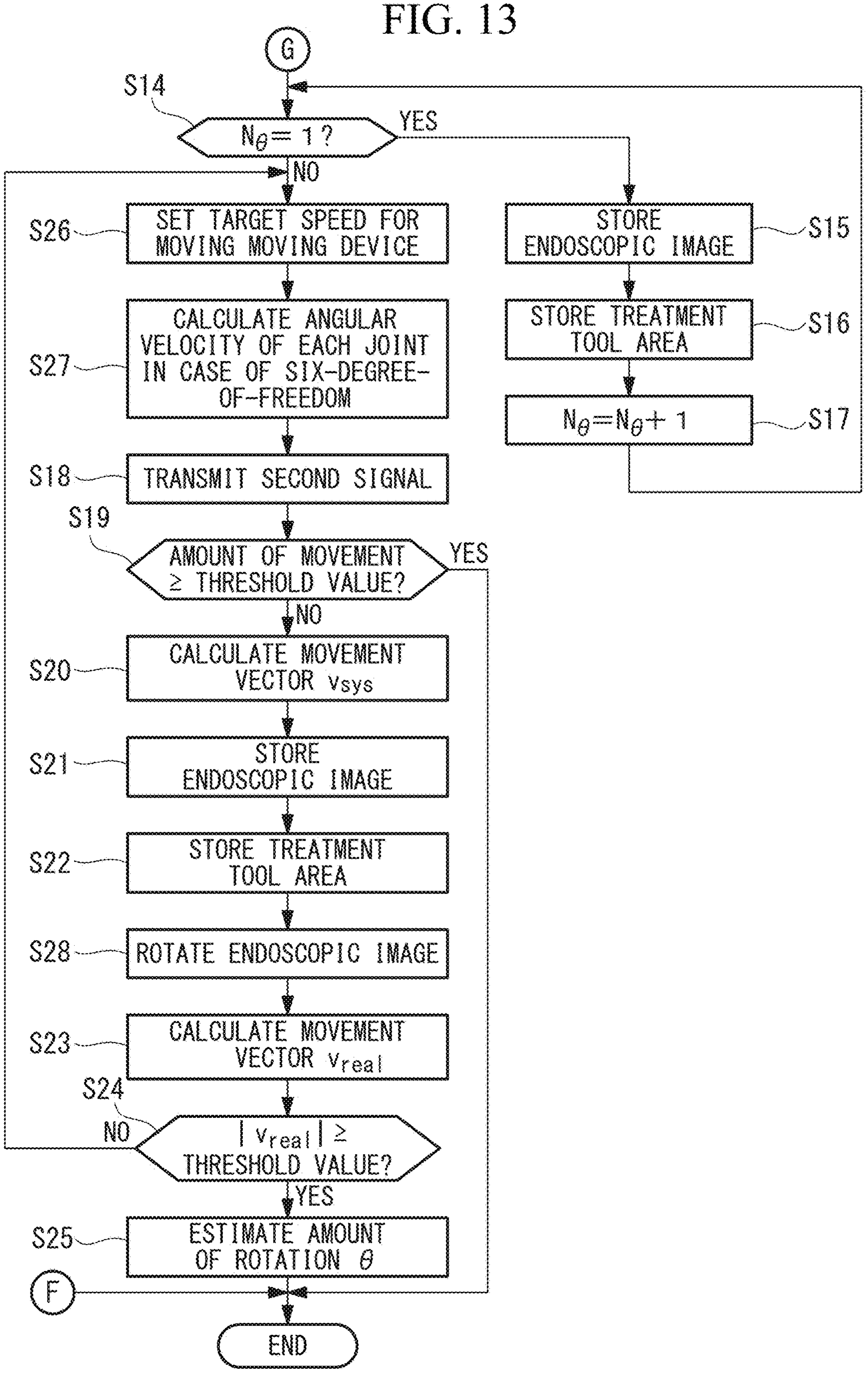
FIG. 13 is a diagram showing a fifth modification of the endoscope system of FIG. 1, and showing a flowchart following FIG. 5A.

Therefore, as shown in FIG. 13, when determining in step S14 that $N_\theta=1$ is satisfied, the processor 5*a* sets a target speed of the distal end of the moving device 3 for operating the moving device 3 (step S26). Based on the set target speed, the processor 5*a* calculates the angular velocity of each of the joints 3M, 3P from inverse kinematics on the assumption that the moving device 3 has six-degree-of-freedom, and calculates a second signal for achieving the calculated angular velocity (step S27).

In this case, a second signal for a joint which rotates the endoscope 2 around the longitudinal axis A, but does not actually exist is also calculated. When the thus-calculated second signal is transmitted to the moving device 3, the entire endoscope 2 would be rotated around the longitudinal axis A to compensate for the posture of the endoscope 2 if the moving device 3 has six-degree-of-freedom. However, the posture of the endoscope 2 is not compensated because the moving device 3 of the present embodiment does not have a driving joint around the longitudinal axis A.

Therefore, the processor 5*a* rotates the endoscopic image C stored in step S21 after the activation of the moving device 3 by only the rotation angle corresponding to the second signal calculated for the joint around the longitudinal axis A which does not actually exist (step S28). As a result, the same endoscopic image C as an endoscopic image C which would be captured when the moving device 3 has the six-degree-of-freedom can be acquired as the endoscopic image C to be captured by the endoscope 2, and at least one of the two endoscopic images C acquired before and after the transmission of the second signal is rotated by image processing so that the angles around the longitudinal axis A of the two endoscopic images C acquired before and after the transmission of the second signal match each other, whereby it is possible to accurately calculate the moving direction of the object S before and after the movement.

(Sixth Modification)

Further, as described above, in the present embodiment, the two joints at the distal end of the moving device 3 are passive joints 3P, and have neither a motor nor an angle sensor. Therefore, when the three driving joints 3M are driven, the lens tube portion 2*a* of the endoscope 2 swings the trocar 8, and is moved along the through-hole 8*a* of the trocar 8 by the reaction force received from the trocar 8. Following this movement, the passive joints 3P are passively activated.

However, as described above, a gap exists between the inner surface of the through-hole 8*a* of the trocar 8 and the outer surface of the lens tube portion 2*a* of the endoscope 2. Therefore, as shown in FIG. 4, in a state where the lens tube portion 2*a* is receiving no reaction force from the trocar 8, even if the endoscope 2 is attempted to be moved in the longitudinal axis direction A by transmitting the first signal, the lens tube portion 2*a* may move in a direction intersecting the longitudinal axis direction A after the movement is started. In this case, since a correct movement vector $v_{obj}$ cannot be obtained, the estimation accuracy of the amount of rotation β of the endoscope 2 deteriorates.

Figure 14:
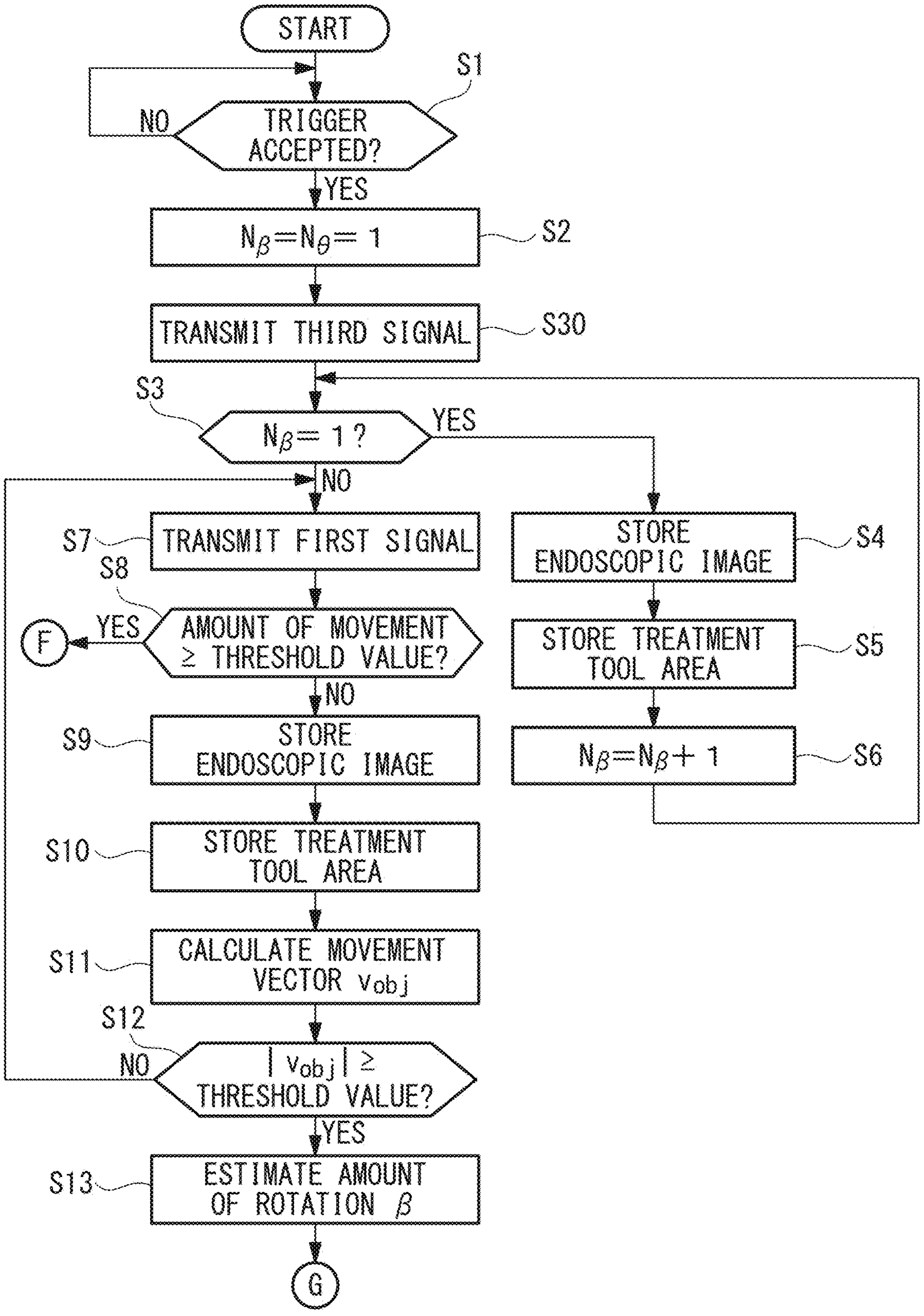
FIG. 14 is a diagram showing a sixth modification of the endoscope system of FIG. 1, and showing a flowchart replacing FIG. 5A.
Figure 15:
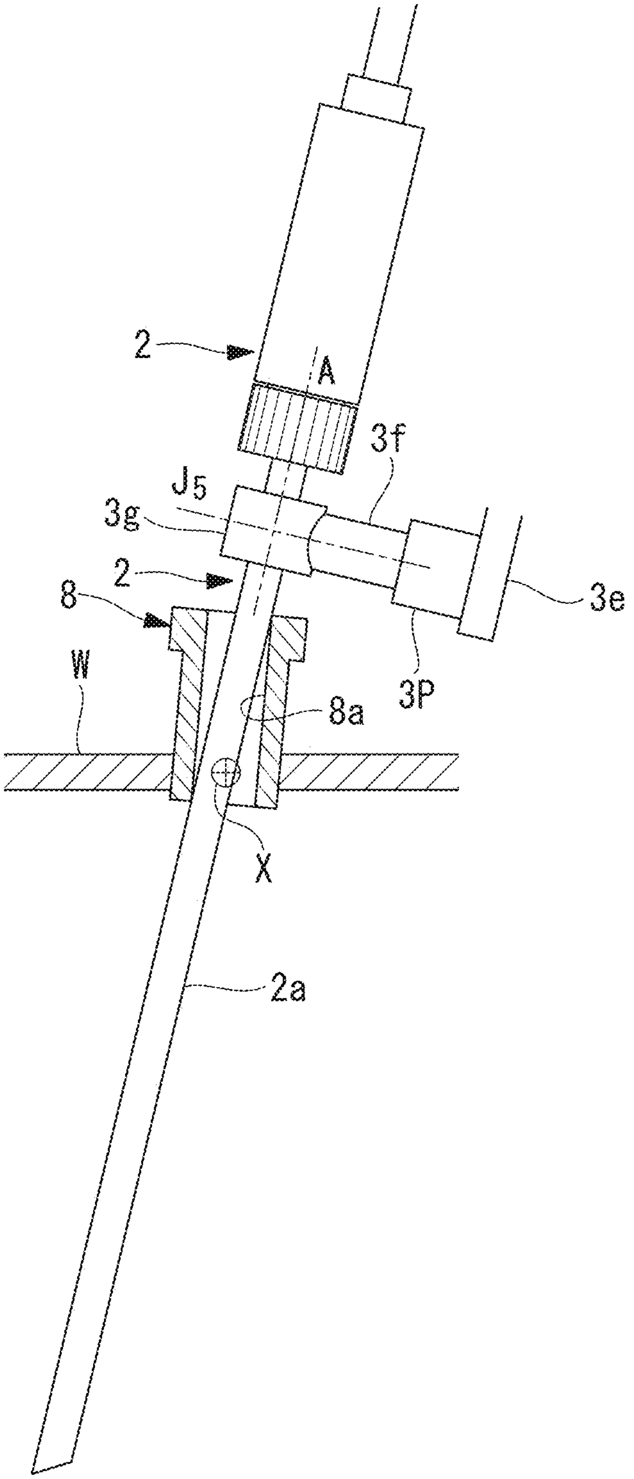
FIG. 15 is a diagram illustrating an operation of a moving device according to a third signal in the flowchart of FIG. 14.

Therefore, as shown in FIG. 14, before acquiring the first endoscopic image C, the processor 5*a* transmits a third signal to the moving device 3 (step S30) to move the endoscope 2 to a position where the lens tube portion 2*a* receives a reaction force equal to or more than a predetermined threshold value from the trocar 8. For example, by transmitting the third signal, the inclination angle of the lens tube portion 2*a* may be changed as shown in FIG. 15 to elastically deform a sealing member (not shown) between the lens tube portion 2*a* and the through-hole 8*a* and/or the abdominal wall W, thereby generating a reaction force equal to or more than a predetermined threshold value. Thereafter, by executing the processing from step S3, it is possible to estimate the amount of rotation β with high accuracy.

(Seventh Modification)

Further, in a case where the moving device 3 has the passive joint 3P, a problem may occur when the amount of rotation θ of the endoscope 2 is estimated. In other words, when there is a gap between the lens tube portion 2*a* and the through-hole 8*a* of the trocar 8, there may occur a situation that even if an attempt is made to move the endoscope 2 straight in a direction perpendicular to the longitudinal axis A, the passive joint 3P shifts unrestrainedly by the amount corresponding to the gap, so that the passive joint 3P cannot be moved straight.

Figure 16:
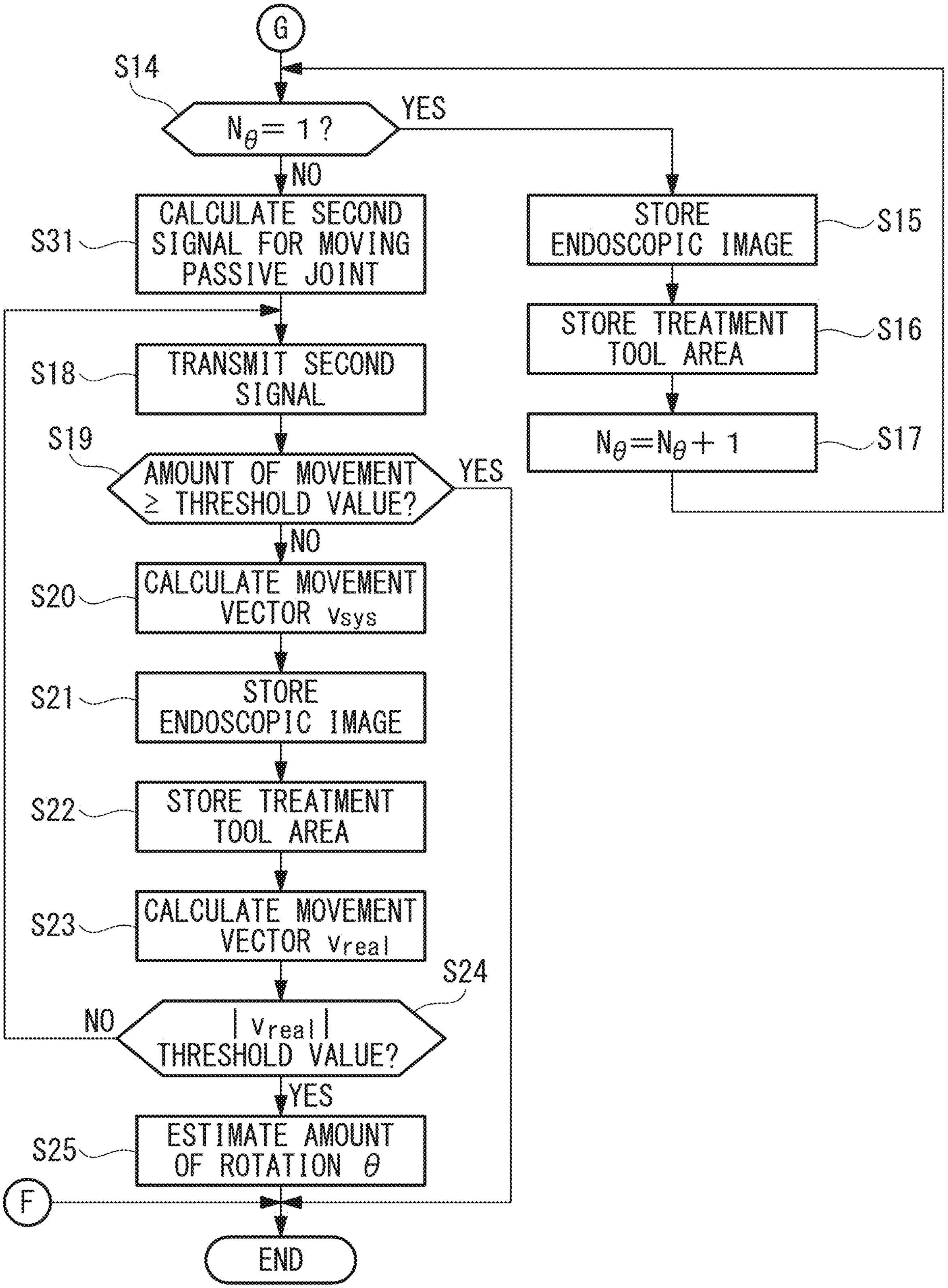
FIG. 16 is a diagram showing a seventh modification of the endoscope system of FIG. 1, and showing a flowchart following FIG. 5A.

Therefore, as shown in FIG. 16, when it is determined in step S14 that $N_\theta=1$ is not satisfied, the processor 5*a* calculates a second signal for achieving a moving direction of the endoscope 2 which allows the passive joint 3P to move in order to move the endoscope 2 straight (step S31). The processor 5*a* may transmit the thus-calculated second signal to the moving device 3.

Since the endoscope 2 is moved in the direction in which the passive joint 3P moves, the endoscope 2 can be moved straight in the direction perpendicular to the longitudinal axis A, and the accuracy of estimating the amount of rotation θ can be improved.

(Eighth Modification)

Figure 17:
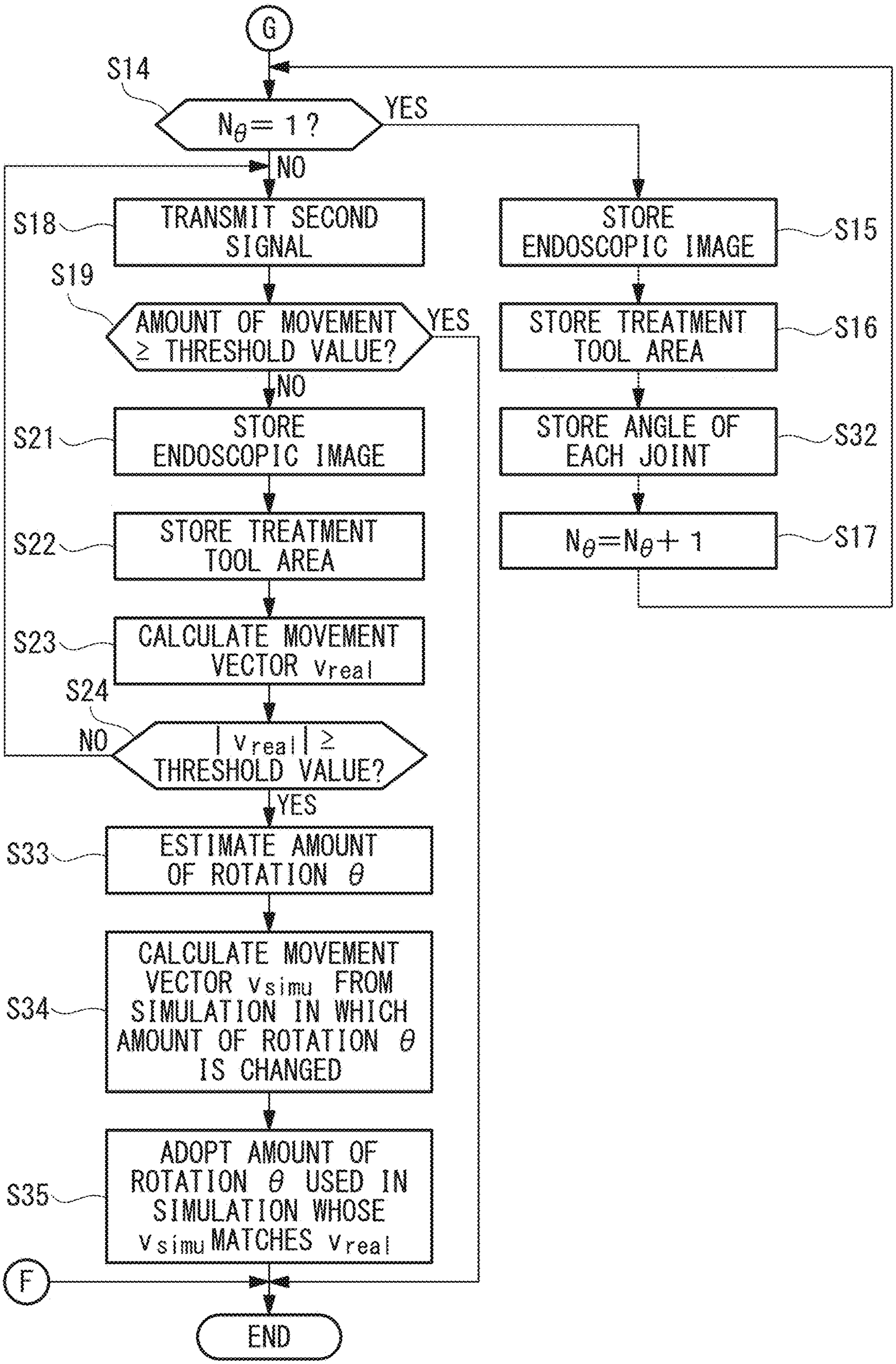
FIG. 17 is a diagram showing an eighth modification of the endoscope system of FIG. 1, and showing a flowchart following FIG. 5A.
Figure 18:
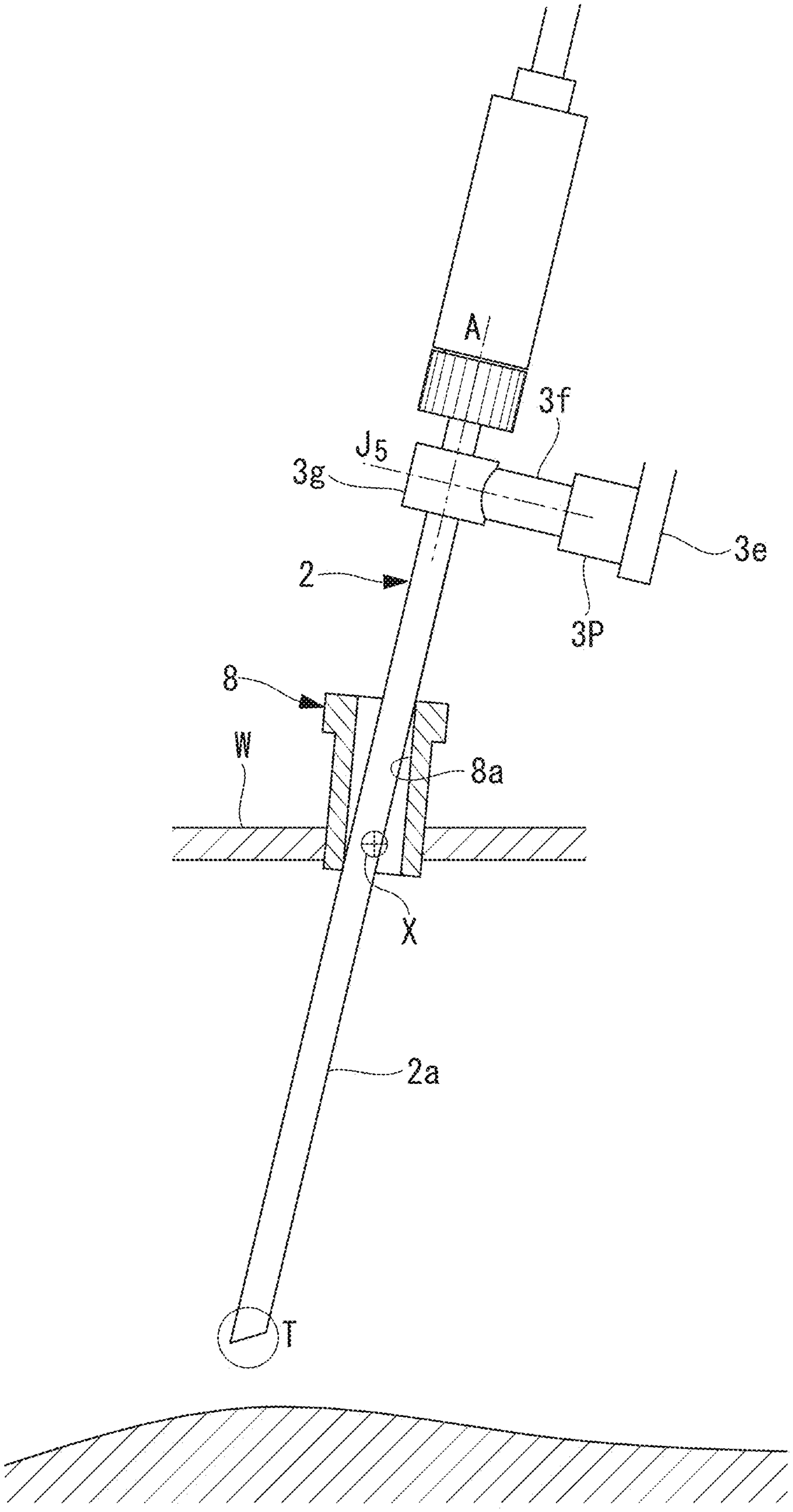
FIG. 18 is a partial longitudinal sectional view of an endoscope and a trocar that shows a ninth modification of the endoscope system of FIG. 1.

Further, in the present embodiment, in step S20, the assumed movement vector $v_{sys}$ is calculated, and in step S25, the intersection angle between the movement vector $v_{sys}$ and the estimated movement vector $v_{real}$ is estimated as the amount of rotation θ of the endoscope 2. Instead of this, as shown in FIG. 17, the processor 5*a* may perform simulation for a plurality of amounts of rotation θ, calculate the movement vector of the object S on the endoscopic image C, and adopt, as an estimation result, the amount of rotation θ used in the simulation in which the moving direction matches that of the real movement vector $v_{real}$.

In other words, first, the processor 5*a* stores the angle of each driving joint 3M of the moving device 3 at the time when the first endoscopic image C and the treatment tool area D are stored in steps S15 and S16 (step S32). Then, at the time point when the real movement vector $v_{real}$ having sufficient magnitude is calculated, the processor 5*a* stores the angle of each driving joint 3M of the moving device 3 again (step S33). Thereafter, the processor 5*a* calculates respective movement vectors $v_{simu}$ of the object S through simulations in which the amount of rotation θ is changed (step S34). The processor 5*a* selects a simulation in which a movement vector $v_{simu}$ whose moving direction matches that of the real movement vector $v_{real}$ is calculated, and adopts the amount of rotation θ used in the selected simulation as an estimated value (step S35).

In the simulation, the angle of each of the joints 3M stored in steps S32 and S33, the amounts of rotation β estimated in step S13, the length of each of the links 3*b*, 3*c*, and 3*d*, and the distance from the distal end of the endoscope 2 to the object S are used as fixed values. Then, the processor 5*a* performs a plurality of simulations to calculate the movement vector $v_{simu}$ of the object S using the amount of rotation θ as a parameter.

According to the present embodiment, since the simulation is performed using the real angles of the driving joints 3M of the moving device before and after movement, it is possible to calculate the movement vector $v_{simu}$ in consideration of the variation in posture of the endoscope 2 caused by the moving device having five-degree-of-freedom and including the passive joints 3P. Therefore, as compared with the movement vector $v_{sys}$ of the first embodiment which is calculated on the assumption that the distal end of the endoscope 2 moves straight in the direction perpendicular to the longitudinal axis A, the movement vector $v_{simu}$ can be calculated with high accuracy, and the estimation accuracy of the amount of rotation θ can be improved.

Further, the case where the sixth to eighth modifications are implemented individually has been described, but instead of this case, the modifications may be implemented while combining at least two of these modifications.

(Ninth modification)

Furthermore, when the endoscope 2 is inserted via the trocar 8 as described above, if the endoscope 2 is excessively advanced along the longitudinal axis A in order to estimate the amount of rotation β, it is considered the distal end of the endoscope 2 comes into contact with the object S inside the abdominal cavity. On the other hand, if the endoscope 2 is excessively retreated along the longitudinal axis A, it is considered that the distal end of the endoscope 2 enters the trocar 8, and sufficient optical flow cannot be obtained.

Therefore, the operator operates the moving device 3 while checking the endoscopic image C in advance, moves the endoscope 2 to a position and posture in which the distal end thereof does not come into contact with the object S inside the body cavity, and registers the three-dimensional position of the distal end of the endoscope 2 at that time as a registration point T. The processing of estimating the amount of rotation β may be performed by moving the endoscope 2 in a retreating direction along the longitudinal axis A from a state in which the distal end of the endoscope 2 is disposed at the registration point T.

Figure 19:
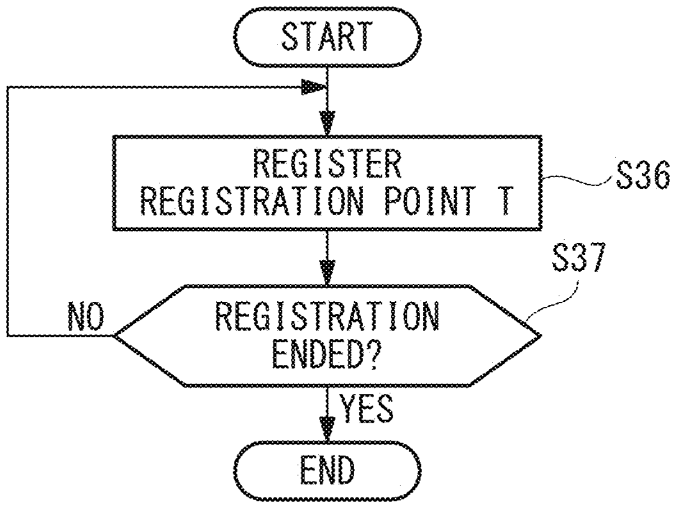
FIG. 19 is a flowchart illustrating registration processing of a registration point in the endoscope system of FIG. 18.
Figure 20:
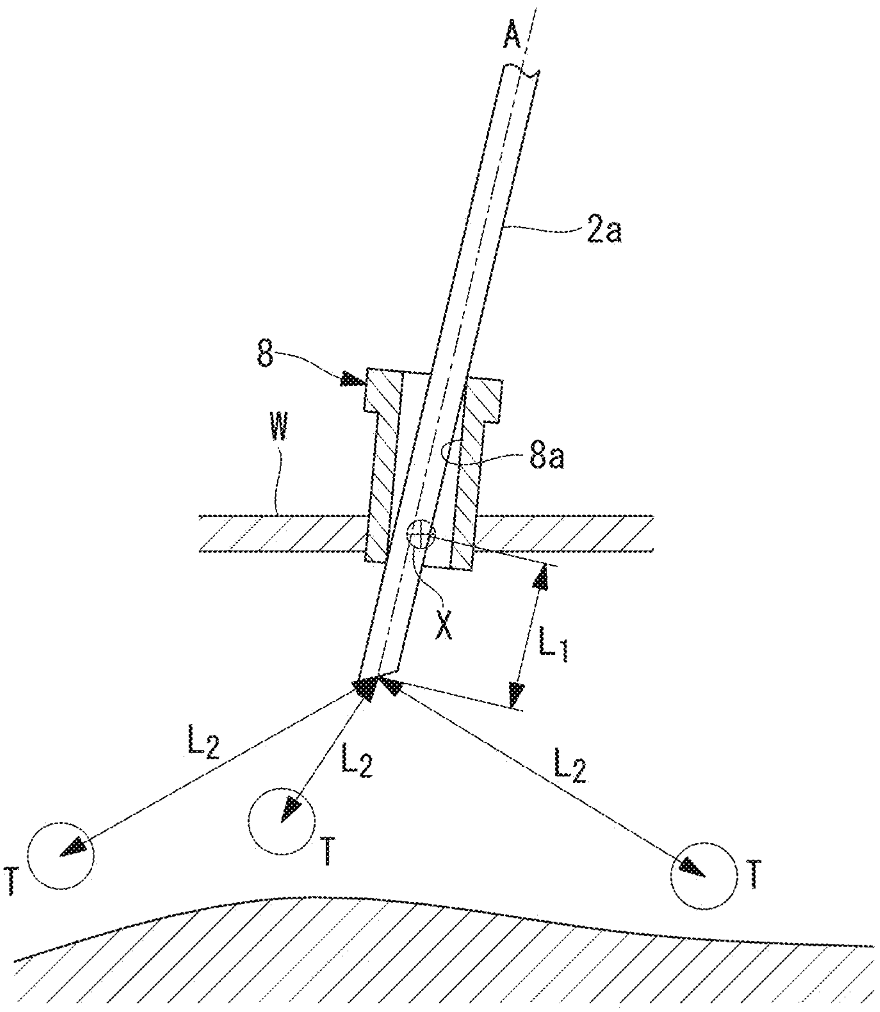
FIG. 20 is a diagram illustrating the distances between the distal end of the endoscope and a plurality of registration points and a pivot point in the endoscope system of FIG. 18.

Specifically, as shown in FIG. 19, the processor 5*a* registers the three-dimensional position of the distal end of the endoscope 2 as a registration point T (step S36). The number of registration points T may be one or more. As shown in FIG. 20, when registering a plurality of registration points T, the processor 5*a* determines whether the registration is terminated (step S37), and repeats the processing of step S36 at an arbitrary number of times.

Figure 21:
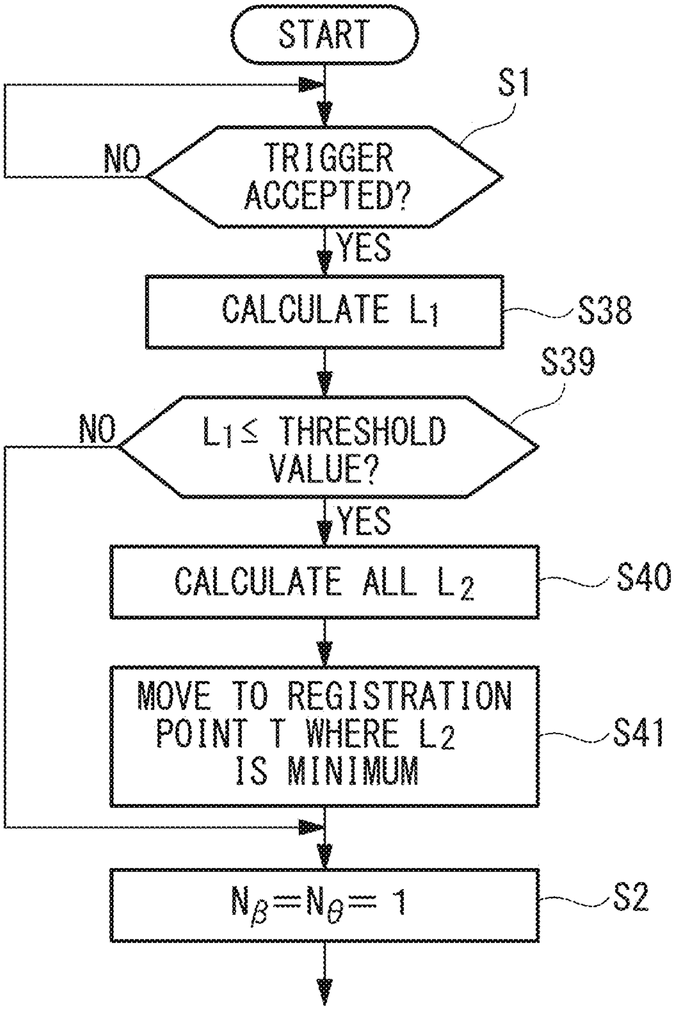
FIG. 21 is a diagram showing a flowchart replacing FIG. 5A of the endoscope system of FIG. 18.

When the processing of estimating the amounts of rotation β and θ is started in a state where the distal end of the endoscope 2 is disposed at an arbitrary position, as shown in FIG. 21, the processor 5*a* calculates a distance $L_1$ between the distal end of the endoscope 2 and the pivot point X (step S38). Then, the processor 5*a* determines whether the distance $L_1$ is equal to or less than a threshold value (step S39), and if the distance $L_1$ is larger than the threshold value, the processor 5*a* executes the processing from step S2. In this case, the operating direction of the moving device 3 according to the first signal transmitted in step S7 may be either the direction in which the endoscope 2 is advanced along the longitudinal axis A or the direction in which the endoscope 2 is retreated.

When it is determined in step S39 that the distance $L_1$ is equal to or less than the threshold value, the processor 5*a* calculates a distance $L_2$ between the distal end of the endoscope 2 and the registration point T for all registration points T (step S40). Then, the processor 5*a* moves the distal end of the endoscope 2 to the registration point T which provides the smallest calculated distance $L_2$ (step S41), and then executes the processing from step S2. In this case, the operating direction of the moving device 3 according to the first signal transmitted in step S7 is limited to the direction in which the endoscope 2 is retreated along the longitudinal axis A.

As described above, according to the present embodiment, in the processing of estimating the amount of rotation β, it is possible to prevent occurrence of the inconvenience of entering the trocar 8 and efficiently estimate the amount of rotation β. In particular, simply by registering the registration points T, the estimation processing can be performed regardless of the position of the distal end of the endoscope 2 at the time of starting the estimation. Therefore, there is an advantage that the operator does not have to manually move the endoscope 2 to a position where the distance $L1_1$ is ensured to be larger than the threshold value each time.

Furthermore, when the distal end of the endoscope 2 is moved to the registration point T by the operation of the moving device 3, the processor 5*a* moves the distal end of the endoscope 2 as follows. First, the endoscope 2 is retreated along the longitudinal axis A until the distance $L_1$ between the distal end of the endoscope 2 and the pivot point X becomes a constant distance or less. Next, the posture of the endoscope 2 is adjusted so that the longitudinal axis A of the endoscope 2 is parallel to a straight line connecting a registration point T to which the endoscope 2 is requested to be moved and the pivot point X. Finally, the endoscope 2 is moved along the longitudinal axis A until the distal end of the endoscope 2 is at a distance equal to or less than a predetermined threshold value from the registration point T. As a result, even when there is an obstacle such as tissue or a treatment tool between the distal end of the endoscope 2 and the registration point T to which the endoscope 2 is requested to be moved at the start time of the processing of estimating the amount of rotation β, it is possible to move the distal end of the endoscope 2 to the registration point T without causing the distal end of the endoscope 2 to come into contact with the obstacle.

Moreover, in the present embodiment, the moving device 3 including three driving joints 3M and two passive joints 3P has been described. Instead of this moving device 3, a moving device 3 including five or more driving joints 3M may be adopted. As a result, the position and posture of the endoscope 2 can be controlled more accurately. However, since the driving joint 3M requires a motor and an angle sensor, the moving device 3 becomes larger in size. Therefore, according to the present embodiment, the minimum number of driving joints 3M that can achieve the position and posture of the endoscope 2 are provided, so that the moving device 3 can be miniaturized and the moving device 3 can be prevented from interfering with surgery.

Furthermore, in the present embodiment, the imaging element 2*e* in the camera head 2*c* is arranged so as to be orthogonal to the longitudinal axis A of the lens tube portion 2*a* and such that the longitudinal axis A passes through the center of the imaging surface. Instead of this, in a case where an optical axis B is inclined by the optical element 2*b* such as a mirror or a prism in the camera head 2*c*, the imaging element 2*e* may be arranged so as to be perpendicular to the optical axis B which is inclined with respect to the longitudinal axis A and such that the optical axis B passes through the center of the imaging surface.

Second Embodiment

Next, an endoscope system 1, an endoscope movement control device 5, a method, a program, and a recording medium according to a second embodiment of the present disclosure will be described. In the present embodiment, points different from the first embodiment will be described, and with respect to configurations common to the first embodiment, the same reference signs are appended, and description thereof will be omitted.

Figure 22:
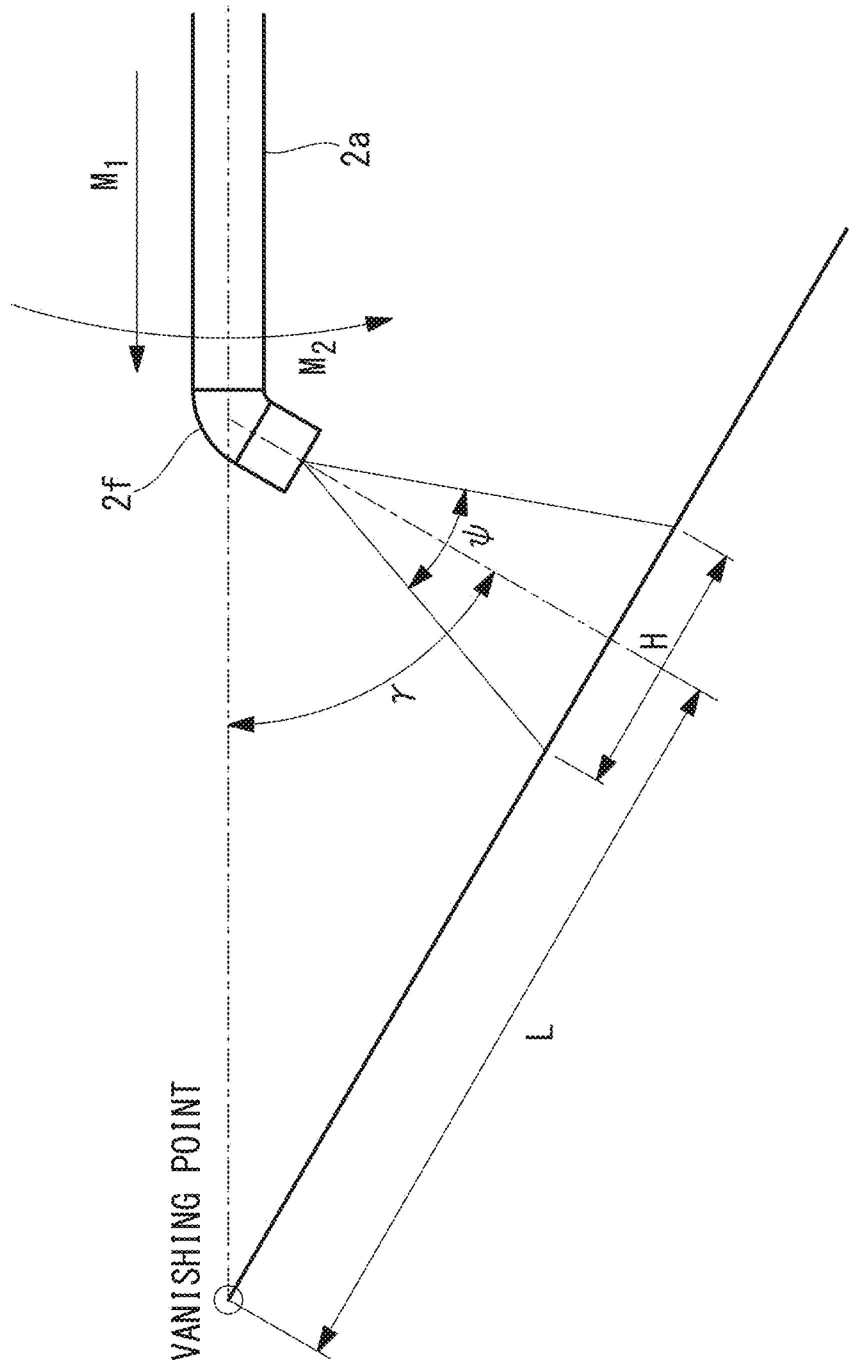
FIG. 22 is a diagram showing the relation of an angle of a curved joint of an endoscope, an angle of view, and a vanishing point in an endoscope system according to a second embodiment of the present disclosure.
Figure 23:
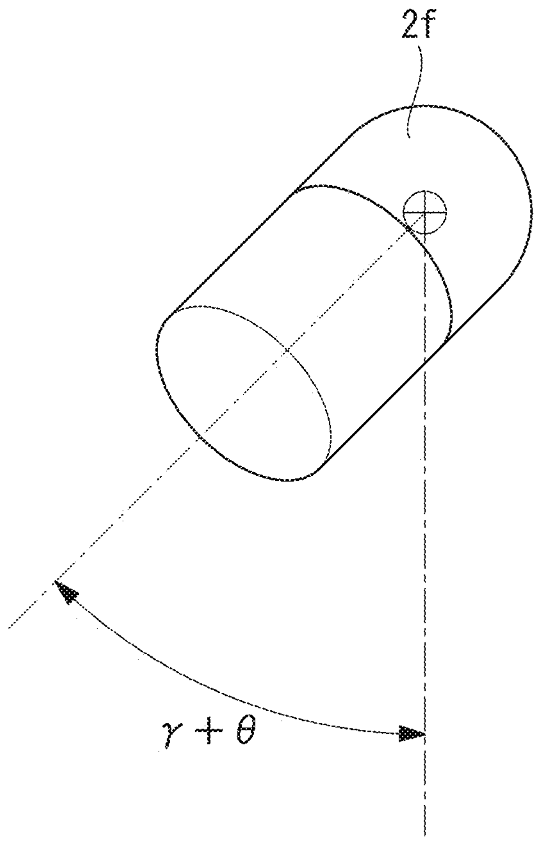
FIG. 23 is a diagram illustrating the amount of rotation about the longitudinal axis of the endoscope in the endoscope system of FIG. 22.

The endoscope system 1 according to the present embodiment is different from the first embodiment in that the endoscope 2 has a two-degree-of-freedom curved joint 2*f* at the distal end of the lens tube portion 2*a* as shown in FIG. 22 and FIG. 23 instead of the optical element 2*b* which is provided in the lens tube portion 2*a* to incline the visual axis B. Since the curved joint 2*f* has two-degree-of-freedom, there is no operation ring 2*d* for rotating the inclined direction of the visual axis B around the longitudinal axis A by the optical element 2*b*.

In the description of the present embodiment, as shown in FIG. 22, an inclination angle of the visual axis B with respect to the longitudinal axis A of the lens tube portion 2*a* due to the curvature of the curved joint 2*f* is defined as an amount of rotation γ, and as shown in FIG. 23, an angle which indicates the bending direction of the curved joint 2*f* with the longitudinal axis A as the center is defined as an amount of rotation δ. The two-degree-of-freedom of the curved joint 2*f* of the endoscope 2 is defined by these amounts of rotation γ and δ. Further, similarly to the first embodiment, the amount of rotation θ is an attachment angle of the lens tube portion 2*a* of the endoscope 2 to the holder 3*g*, and it can be arbitrarily changed manually by the operator without using the moving device 3.

In the endoscope system 1 according to the present embodiment, the processor 5*a* executes a program (endoscope movement control program) which is recorded in the storage unit 5*c* and read out to the memory 5*b*, thereby estimating the amounts of rotation γ, δ, and θ of the endoscope 2.

An endoscope movement control method using the endoscope system 1 according to the present embodiment will be described below with reference to the drawings.

Figure 24:
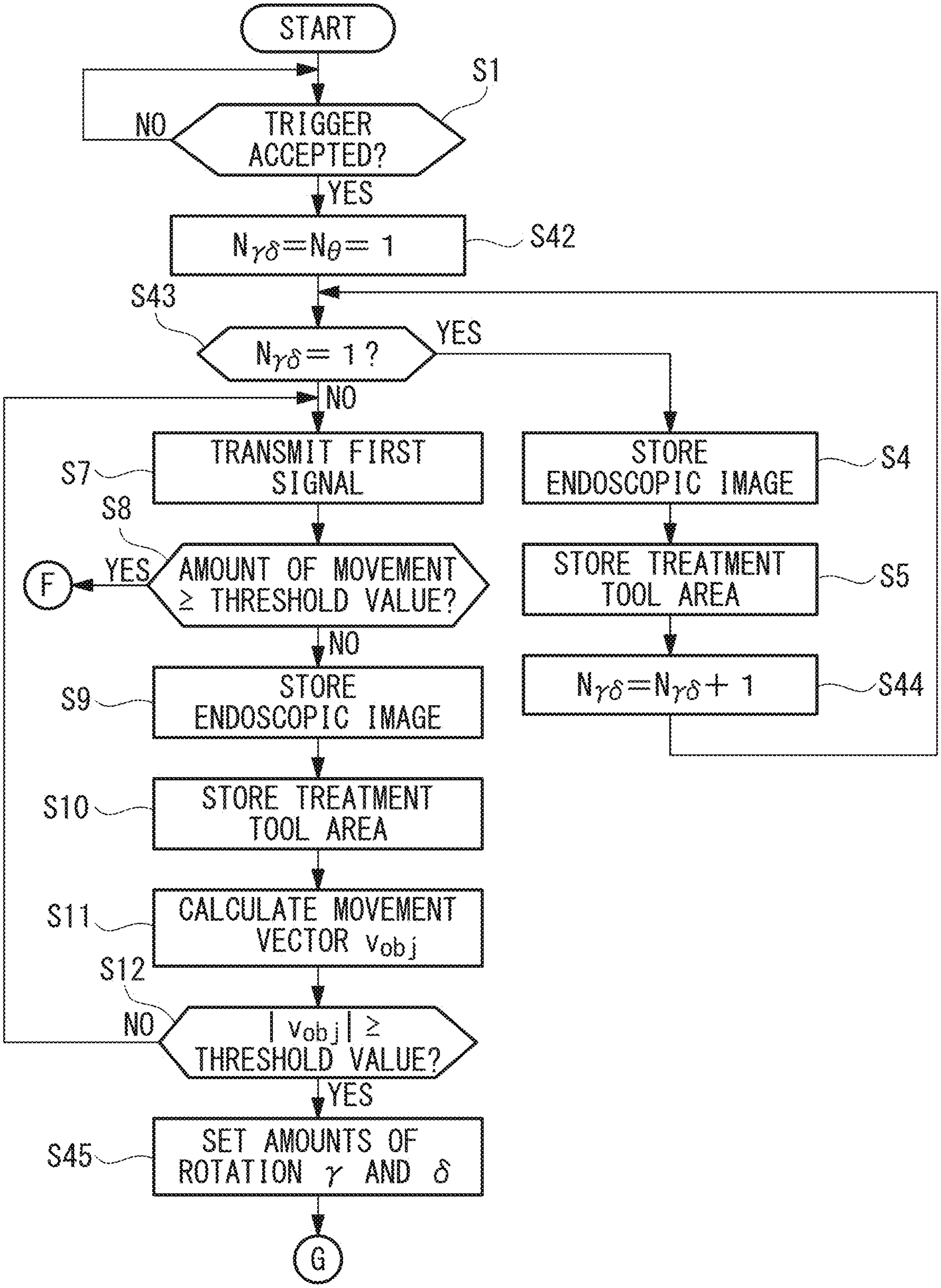
FIG. 24 is a diagram showing a flowchart replacing FIG. 5A of the endoscope system of FIG. 22.

As shown in FIG. 24, the endoscope movement control method according to the present embodiment is different in that the number of loops $N_{\gamma\delta}$ is used instead of the number of loops $N_\beta$ in steps S42, S43, and S44, but the processing up to step S12 is performed in the same manner as in the first embodiment.

The present embodiment differs from the first embodiment in estimating the amounts of rotation γ and δ (step S45).

The amount of rotation γ can be determined by setting θ=0° and calculating Formula (3) using the distance L between the vanishing point and the image center O in the positional relation shown in FIG. 22.

[Formula 3]

$$\gamma = \tan^{-1}\left(\frac{2 \cdot L \cdot \tan(\psi/2)}{H}\right) \tag{3}$$

Here, the distance L is determined as follows.

Figure 25:
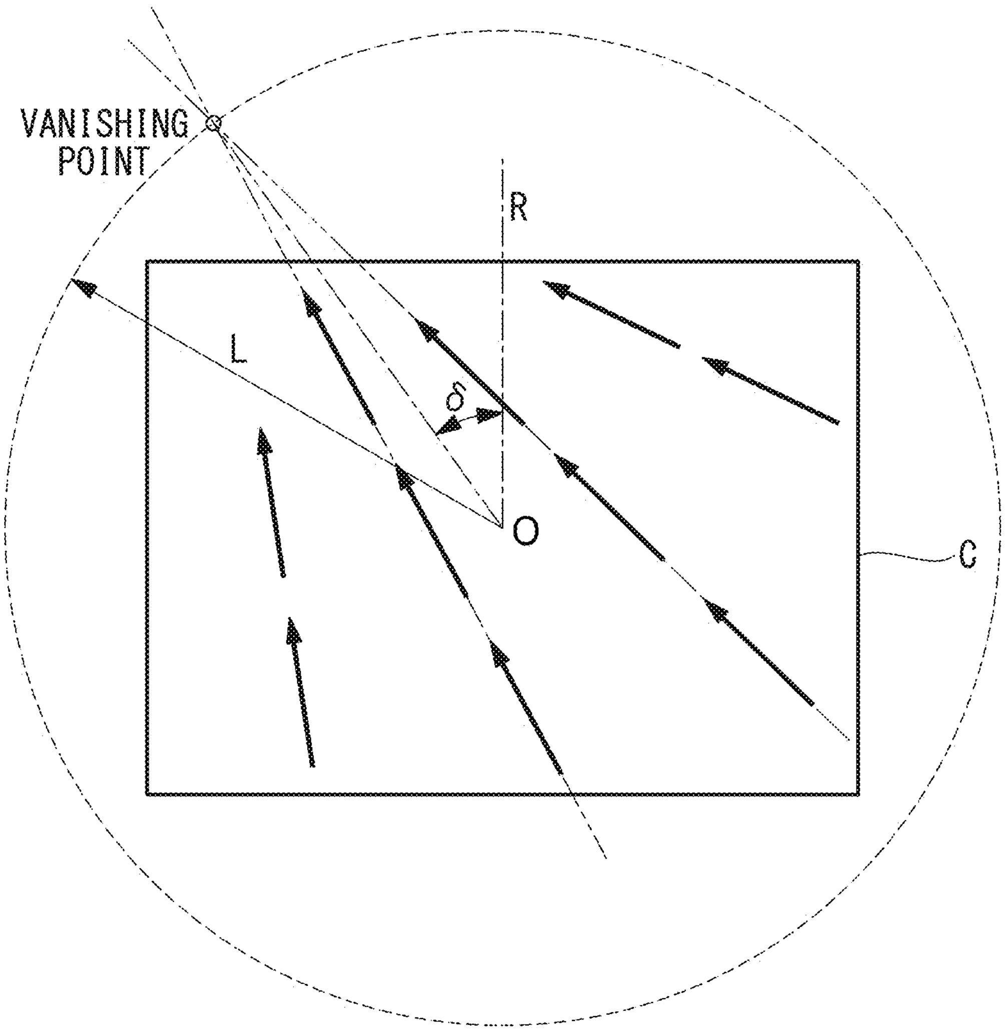
FIG. 25 is a diagram illustrating processing for determining the distance between the center of an image and a vanishing point and the amount of rotation in the endoscope system of FIG. 22.

First, as shown in FIG. 25, an equation of a straight line indicating the direction of each vector is determined using movement vectors $v_{obj}$ of two or more feature points on the endoscopic image C calculated in step S11. From the equations of these straight lines, the intersection point of the straight lines is determined as a vanishing point. As a result, the distance L from the image center O to the vanishing point is determined.

The amount of rotation γ can be estimated by substituting the determined distance L into Formula (3). Further, the angle of a straight line connecting the calculated vanishing point and the image center O with respect to the reference line R can be estimated as the amount of rotation δ. Further, the amount of rotation θ can be estimated in the same manner as in the first embodiment.

As described above, according to the present embodiment, it is possible to estimate the amounts of rotation γ and θ of the two-degree-of-freedom of the curved joint 2*f* of the endoscope 2 to be manually adjusted by the operator, and the attachment angle of the endoscope 2 to be manually adjusted, and correct the holder coordinate system Σr using the estimated amounts of rotation γ, δ, and θ. Therefore, even when the endoscope 2 has a curved joint 2*f*, the operator can intuitively and accurately move the endoscope 2 in a desired direction by operating the user interface 4*a* while observing the endoscopic image C.

REFERENCE SIGNS LIST

1 Endoscope system
2 Endoscope
2*a* Lens tube portion (insertion portion)
2*b* Optical system (optical element)
2*c* Camera Head
2*d* Operation ring
2*e* Imaging element
3 Moving device (robotic arm)
3M Driving joint (joint)
3P Passive joint
5 Control device (endoscope movement control device)
5*a* Processor
8 Trocar
S Object
A Longitudinal axis
B Optical axis
$M_1$ First moving direction
$M_2$ Second moving direction
β First amount of rotation
θ Second amount of rotation

The invention claimed is:

1. An endoscope system comprising:
an endoscope comprising:
an insertion portion extending in a direction of a longitudinal axis;
an imaging sensor disposed at a proximal end of the insertion portion, wherein the insertion portion and the imaging sensor are rotatable relative to each other about the longitudinal axis; and
an optical element provided in the insertion portion to tilt an optical axis relative to the longitudinal axis;
a robotic arm that moves and holds the endoscope such that the endoscope is rotatable about the longitudinal axis; and
at least one processor comprising hardware, wherein the processor is configured to:
transmit, to the robotic arm, a first signal for moving the endoscope in the direction of the longitudinal axis,
detect a first moving direction of an object within first two images by using the first two images captured by the imaging sensor before and after movement of the endoscope in the direction of the longitudinal axis,
estimate a direction of the optical axis based on the first moving direction,
determine a first amount of rotation about the longitudinal axis between the insertion portion and the imaging sensor based on the direction of the optical axis,
transmit, to the robotic arm, a second signal for moving the endoscope in a direction perpendicular to the longitudinal axis,
detect a second moving direction of the object within second two images by using the second two images captured by the imaging sensor before and after movement of the endoscope in the direction perpendicular to the longitudinal axis, and
estimate a second amount of rotation about the longitudinal axis between the robotic arm and the endoscope based on the second moving direction and the first amount of rotation.

2. The endoscope system according to claim 1, wherein the at least one processor is configured to:
detect moving directions of a plurality of feature points of the object in the images as first moving directions,
calculate a position of an intersection point of straight lines of the plurality of feature points along the first moving directions respectively, and
estimate the first amount of rotation based on the position of the intersection point.

3. The endoscope system according to claim 1, wherein the at least one processor is configured to estimate the second amount of rotation based on a difference between the second moving direction and a direction in which the robotic arm moves due to the transmission of the second signal.

4. The endoscope system according to claim 1, wherein the at least one processor is configured to:
calculate a moving direction of the object in the second two images due to the transmission of the second signal by a plurality of simulation patterns using the second amount of rotation as a variable parameter, and
estimate, as the second amount of rotation, a value of the variable parameter in a simulation result which matches the second moving direction.

5. The endoscope system according to claim 1, wherein the imaging sensor includes an imaging surface disposed orthogonally to the longitudinal axis, and the longitudinal axis passes through an imaging center of the imaging surface.

6. The endoscope system according to claim 5, wherein the robotic arm includes a plurality of joints, and at least one of the plurality of joints is driven with a signal from the processor, to move a distal end of the insertion portion to a predetermined position in a three-dimensional space, and at the same time, control a posture of the insertion portion except for rotation about the longitudinal axis.

7. The endoscope system according to claim 6, wherein the at least one processor is configured to:

rotate at least one of the second two images captured before and after the transmission of the second signal by image processing such that angles about the longitudinal axis of the second two images captured before and after the transmission of the second signal match each other, and detect the second moving direction.

8. The endoscope system according to claim 6, wherein the plurality of joints includes three active joints driven with the signal, and two passive joints, the insertion portion is inserted into a trocar, and the processor is configured to:

transmit a third signal to the robotic arm to change an inclination angle in the direction of the longitudinal axis until the insertion portion receives a reaction force equal to or more than a predetermined threshold value from the trocar, and detect the first moving direction.

9. The endoscope system according to claim 6, wherein the endoscope includes an operation ring fixed to the insertion portion, and the first amount of rotation is an amount of change in a rotation angle of the operation ring about the longitudinal axis relative to the imaging sensor.

10. The endoscope system according to claim 1, wherein the at least one processor is configured to calculate the first moving direction and the second moving direction using optical flow.

11. The endoscope system according to claim 1, wherein the robotic arm has 6-degrees of freedom.

12. An endoscope movement control method for controlling a robotic arm for moving an endoscope, comprising:

moving the endoscope in a direction of a longitudinal axis of an insertion portion of the endoscope by the robotic arm after transmitting a first signal to the robotic arm, the insertion portion extending in the direction of the longitudinal axis;

detecting a first moving direction of an object in first two images by using the first two images captured by an imaging sensor before and after movement of the endoscope in the direction of the longitudinal axis, the imaging sensor being disposed at a proximal end of the insertion portion, wherein the insertion portion and the imaging sensor are rotatable relative to each other about the longitudinal axis, and the robotic arm holds the endoscope such that the endoscope is rotatable about the longitudinal axis;

estimating a direction of an optical axis based on the first moving direction, the optical axis being tilted relative to the longitudinal axis by an optical element that is provided in the insertion portion;

determining a first amount of rotation about the longitudinal axis between the insertion portion and the imaging sensor based on the direction of the optical axis;

moving the endoscope in a direction perpendicular to the longitudinal axis by the robotic arm after transmitting a second signal to the robotic arm;

detecting a second moving direction of the object in second two images using two images captured by the imaging sensor before and after movement of the endoscope in the direction perpendicular to the longitudinal axis; and estimating a second amount of rotation about the longitudinal axis between the robotic arm and the endoscope based on the second moving direction and the first amount of rotation.

13. The endoscope movement control method according to claim 12, further comprising:

detecting moving directions of a plurality of feature points of the object in the images as first moving directions, calculating a position of an intersection point of straight lines of the plurality of feature points along the first moving directions respectively, and estimating the first amount of rotation based on the position of the intersection point.

14. The endoscope movement control method according to claim 12, further comprising:

estimating the second amount of rotation based on a difference between the second moving direction and a direction in which the robotic arm moves due to the transmission of the second signal.

15. The endoscope movement control method according to claim 12, further comprising:

calculating a moving direction of the object in the second two images due to the transmission of the second signal by a plurality of simulation patterns using the second amount of rotation as a variable parameter, and estimating, as the second amount of rotation, a value of the variable parameter in a simulation result which matches the second moving direction.

16. The endoscope movement control method according to claim 12, further comprising:

rotating at least one of the second two images captured before and after the transmission of the second signal by image processing such that angles about the longitudinal axis of the second two images captured before and after the transmission of the second signal match each other, and detecting the second moving direction.

17. A non-transitory computer-readable recording medium in which an endoscope movement control program for controlling a robotic arm for moving an endoscope is stored, the endoscope movement control program causing a computer to:

move the endoscope in a direction of a longitudinal axis of an insertion portion of the endoscope by the robotic arm after transmitting a first signal to the robotic arm, the insertion portion extending in the direction of the longitudinal axis;

detect a first moving direction of an object in first two images by using two images captured by an imaging sensor before and after movement of the endoscope in the direction of the longitudinal axis, the imaging sensor being disposed at a proximal end of the insertion portion, wherein the insertion portion and the imaging sensor are rotatable relative to each other about the longitudinal axis, and the robotic arm holds the endoscope such that the endoscope is rotatable about the longitudinal axis;

estimate a direction of an optical axis based on the first moving direction, the optical axis being tilted relative to the longitudinal axis by an optical element that is provided in the insertion portion;

determine a first amount of rotation about the longitudinal axis between the insertion portion and the imaging sensor based on the direction of the optical axis;

move the endoscope in a direction perpendicular to the longitudinal axis by the robotic arm after transmitting a second signal to the robotic arm;

detect a second moving direction of the object in second two images by using the second two images captured by the imaging sensor before and after movement of the endoscope in the direction perpendicular to the longitudinal axis; and estimate a second amount of rotation about the longitudinal axis between the robotic arm and the endoscope based on the second moving direction and the first amount of rotation.

18. The non-transitory computer-readable recording medium according to claim 17, wherein the endoscope movement control program causes the computer to:

detect moving directions of a plurality of feature points of the object in the images as first moving directions, calculate a position of an intersection point of straight lines of the plurality of feature points along the first moving directions respectively, and estimate the first amount of rotation based on the position of the intersection point.

19. The non-transitory computer-readable recording medium according to claim 17, wherein the endoscope movement control program causes the computer to:

estimate the second amount of rotation based on a difference between the second moving direction and a direction in which the robotic arm moves due to the transmission of the second signal.

20. The non-transitory computer-readable recording medium according to claim 17, wherein the endoscope movement control program causes the computer to:

calculate a moving direction of the object in the second two images due to the transmission of the second signal by a plurality of simulation patterns using the second amount of rotation as a variable parameter, and estimate, as the second amount of rotation, a value of the variable parameter in a simulation result which matches the second moving direction.

* * * * *